(12) United States Patent
Foust et al.

(10) Patent No.: US 11,382,995 B2
(45) Date of Patent: Jul. 12, 2022

(54) HAND SANITIZING AQUEOUS OZONE SPRAY CHAMBER

(71) Applicant: 3Oe Scientific, LLC, Carmel, IN (US)

(72) Inventors: Thomas F. Foust, Carmel, IN (US); Christopher Thompson, Fort Worth, TX (US); John Morici, Kildeer, IL (US); David Carlson, Lake Zurich, IL (US); Jake Vail, Lake Zurich, IL (US)

(*) Notice: Subject to any disclaimer, the term of this patent is extended or adjusted under 35 U.S.C. 154(b) by 0 days.

(21) Appl. No.: 17/384,621

(22) Filed: Jul. 23, 2021

(65) Prior Publication Data
US 2022/0023453 A1    Jan. 27, 2022

Related U.S. Application Data

(60) Provisional application No. 63/056,299, filed on Jul. 24, 2020, provisional application No. 63/056,538, filed on Jul. 24, 2020.

(51) Int. Cl.
*A61L 2/18*     (2006.01)
*C02F 1/00*     (2006.01)
(Continued)

(52) U.S. Cl.
CPC ............ *A61L 2/183* (2013.01); *A61L 2/0088* (2013.01); *A61L 2/0094* (2013.01); *A61L 2/202* (2013.01); *A61L 2/26* (2013.01); *C02F 1/008* (2013.01); *C02F 1/4672* (2013.01); *C02F 1/46104* (2013.01); *C02F 1/78* (2013.01); *A61L 2202/11* (2013.01); *A61L 2202/122* (2013.01); *A61L 2202/14* (2013.01); *A61L 2202/15* (2013.01); *A61L 2202/17* (2013.01);
(Continued)

(58) Field of Classification Search
CPC .......... A61L 2/0094; A61L 2/202; A61L 2/26; A61L 2202/122; A61L 2202/15
See application file for complete search history.

(56) References Cited

U.S. PATENT DOCUMENTS 3,421,999 A    1/1969  Corwin
4,179,616 A   12/1979  Coviello et al.
(Continued)

FOREIGN PATENT DOCUMENTS

BR    112014013734    6/2017
CA         2856196    6/2013
(Continued)

OTHER PUBLICATIONS

Search Report and Written Opinion issued for PCT/US21/43084 dated Nov. 1, 2021.
(Continued)

*Primary Examiner* — Sean E Conley
(74) *Attorney, Agent, or Firm* — Innovation Law Office; Dennis S. Schell

(57) ABSTRACT

An illustrative aqueous ozone sanitizing system for body part, tissue, and instrument sanitizing, including hand rinsing and sanitizing includes a sanitizing chamber, spray devices configured to simultaneously irrigate the entire left and right hand of a user, at least two aqueous ozone generators each fluidly coupled to a subset of the spray devices, and a housing for the sanitizing chamber having an opening for guiding the user's hand orientation and position into the sanitizing chamber.

30 Claims, 25 Drawing Sheets

(51) Int. Cl.
*C02F 1/461* (2006.01)
*C02F 1/467* (2006.01)
*C02F 1/78* (2006.01)
*A61L 2/00* (2006.01)
*A61L 2/20* (2006.01)
*A61L 2/26* (2006.01)

(52) U.S. Cl.
CPC .. *C02F 2201/004* (2013.01); *C02F 2201/006* (2013.01); *C02F 2201/4614* (2013.01); *C02F 2201/4616* (2013.01); *C02F 2201/46135* (2013.01); *C02F 2201/46145* (2013.01); *C02F 2201/782* (2013.01); *C02F 2209/006* (2013.01); *C02F 2209/03* (2013.01); *C02F 2209/04* (2013.01); *C02F 2209/23* (2013.01); *C02F 2209/40* (2013.01); *C02F 2303/04* (2013.01)

(56) References Cited

U.S. PATENT DOCUMENTS

| | | | |
|---|---|---|---|
| 4,200,121 | A | 4/1980 | Walter et al. |
| 5,695,091 | A | 12/1997 | Winnings et al. |
| 5,762,787 | A | 6/1998 | Park et al. |
| 5,779,865 | A | 7/1998 | Schulze et al. |
| 6,115,862 | A | 9/2000 | Cooper et al. |
| 6,135,146 | A | 10/2000 | Koganezawa et al. |
| 6,491,879 | B2 | 12/2002 | Conrad |
| 6,706,243 | B1 | 3/2004 | Sias et al. |
| 7,713,336 | B2 | 5/2010 | Hengsperger et al. |
| 9,486,817 | B2 | 11/2016 | Patton et al. |
| 9,919,939 | B2 | 3/2018 | Rosko et al. |
| 10,640,878 | B2 | 5/2020 | Jonte et al. |
| 10,767,270 | B2 | 9/2020 | Jonte et al. |
| 10,900,921 | B2 | 1/2021 | Brondum et al. |
| 10,947,138 | B2 | 3/2021 | Rosko et al. |
| 2002/0185423 | A1 | 12/2002 | Boyd et al. |
| 2006/0027507 | A1 | 2/2006 | Hensperger et al. |
| 2006/0213924 | A1 | 9/2006 | Ophardt |
| 2008/0227680 | A1 | 9/2008 | Lynn |
| 2008/0237368 | A1 | 10/2008 | Hengsperger et al. |
| 2010/0252415 | A1 | 10/2010 | Lynn |
| 2010/0326472 | A1 | 12/2010 | Glenn et al. |
| 2011/0011736 | A1 | 1/2011 | Yost, III et al. |
| 2011/0247974 | A1 | 10/2011 | Gale et al. |
| 2012/0285825 | A1 | 11/2012 | Benedetto |
| 2013/0031799 | A1* | 2/2013 | Gagnon .......... A47K 10/48 34/526 |
| 2013/0119083 | A1 | 5/2013 | Ophardt et al. |
| 2013/0183749 | A1 | 7/2013 | Aamodt et al. |
| 2013/0195725 | A1* | 8/2013 | Lynn ............... C11D 3/50 422/111 |
| 2013/0206654 | A1 | 8/2013 | Lutz et al. |
| 2013/0224072 | A1 | 8/2013 | Glazer et al. |
| 2014/0027388 | A1 | 1/2014 | Constant |
| 2014/0263689 | A1 | 9/2014 | Patton et al. |
| 2015/0308091 | A1 | 10/2015 | Foust et al. |
| 2015/0335775 | A1* | 11/2015 | Toso ............... B08B 9/0826 422/29 |
| 2016/0339132 | A1 | 11/2016 | Cosman et al. |
| 2017/0137953 | A1 | 5/2017 | Jonte et al. |
| 2017/0260722 | A1 | 9/2017 | Horwitz et al. |
| 2017/0275191 | A1 | 9/2017 | Lutz et al. |
| 2018/0008734 | A1* | 1/2018 | Andersen ............ A61L 2/22 |
| 2018/0214588 | A1 | 8/2018 | Casares |
| 2018/0306430 | A1 | 10/2018 | Weaver et al. |
| 2018/0334752 | A1 | 11/2018 | Oyama et al. |
| 2019/0001006 | A1 | 1/2019 | Rodenbeck et al. |
| 2019/0022263 | A1 | 1/2019 | Quilici |
| 2019/0025273 | A1 | 1/2019 | Brondum et al. |
| 2019/0030204 | A1 | 1/2019 | Jurak et al. |
| 2019/0201566 | A1 | 7/2019 | Hollst |
| 2019/0209719 | A1 | 7/2019 | Andersen et al. |
| 2019/0255205 | A1 | 8/2019 | Cosman et al. |
| 2019/0284066 | A1 | 9/2019 | Mullen et al. |
| 2020/0263312 | A1 | 8/2020 | Jonte et al. |
| 2021/0123875 | A1 | 4/2021 | Brondum et al. |
| 2021/0140904 | A1 | 5/2021 | Brondum et al. |
| 2021/0179461 | A1 | 6/2021 | Rosko et al. |

FOREIGN PATENT DOCUMENTS

| | | |
|---|---|---|
| CA | 2992280 | 1/2017 |
| CA | 2946465 | 5/2017 |
| CA | 3007437 | 6/2017 |
| CA | 2846169 | 8/2018 |
| CH | 669116 | 2/1989 |
| CN | 201495127 | 6/2010 |
| CN | 201760242 | 3/2011 |
| CN | 103987664 | 8/2014 |
| CN | 204120920 | 1/2015 |
| CN | 104826224 | 8/2015 |
| CN | 106967994 | 7/2017 |
| CN | 108264023 | 7/2018 |
| CN | 108946913 | 7/2018 |
| CN | 208791269 | 4/2019 |
| CN | 209220534 | 8/2019 |
| CN | 210528559 | 8/2019 |
| CN | 111419689 | 7/2020 |
| CN | 211005645 | 7/2020 |
| CN | 211024277 | 7/2020 |
| CN | 211559865 | 9/2020 |
| CN | 213048748 | 4/2021 |
| CN | 213231656 | 5/2021 |
| CN | 213251572 | 5/2021 |
| DE | 29518833 | 9/1995 |
| DE | 202020003223 | 8/2020 |
| ES | 1111506 | 11/2011 |
| GB | 767227 | 1/1957 |
| JP | 2002146865 | 11/2000 |
| JP | 2008189968 | 8/2008 |
| JP | 4528840 | 8/2010 |
| JP | 5574877 | 8/2014 |
| JP | 2014201768 | 10/2014 |
| JP | 5925653 | 5/2016 |
| KR | 20110039612 | 4/2011 |
| KR | 101211390 | 12/2012 |
| KR | 101367624 | 3/2014 |
| KR | 20200104630 | 9/2020 |
| KR | 102180182 | 11/2020 |
| KR | 20090045482 | 11/2020 |
| WO | 2011144285 | 11/2011 |
| WO | 2013086217 | 6/2013 |
| WO | 2016210071 | 12/2016 |
| WO | 2017011506 | 1/2017 |
| WO | 2017112795 | 6/2017 |
| WO | 2018100358 | 6/2018 |
| WO | 2021036087 | 3/2021 |

OTHER PUBLICATIONS

Search Report and Written Opinion issued for PCT/US21/043092 dated Nov. 3, 2021.
Search Report and Written Opinion issued for PCT/US21/43079 dated Dec. 28, 2021.
Search and Written Opinion issued for PCT/US21/43069 dated Oct. 29, 2021.
Search and Written Opinion issued for PCT/US21/43066 dated Oct. 29, 2021.
Search and Written Opinion issued for PCT/US21/43091 dated Jan. 31, 2022.
Cleancore Solutions; CCS1000 Ice System; Technical Data Sheet; https:cleancoresol.com/wp-content/uploads/2019/10/19-CCS1000-IceMachine.pdf; Jun. 4, 2020.
Panasonic Key Technologies; Boasting Hight Efficiency Makes It Possible to Miniaturize "Ozone Water" Device; Newsletter Accessed Jul. 19, 2021.
Meritech; CleanTech Automatic Hand Washing Stations; Retrieved from webpage <https://www.meritech.com/products/handwashing-systems>; Jul. 19, 2021.

(56) References Cited

OTHER PUBLICATIONS

Cashido; 10 Second Machine Product Page; Retrieved from the webpage <https://www.cashido.com.tw/en/product/10-Second-Machine/ozone-faucet.html>; Jul. 19, 2021.
Oxidation Technologies, LLC—SB100 Product Page; Retrieved from webpage <https://www.oxidationtech.com/sb100.html>; Jul. 19, 2021.
Deposon; Ozone Sanitizing Sprayer Product Page; Retrieved from webpage <https://www.deposon.com/Ozone-Sanitizing-Sprayer-pd49322496.html>; Jul. 19, 2021.
Panasonic; YouTube video illustrating the structure of Panasonic's "Ozone Water" device; Retrieved from <https://www.youtube.com/watch?v=ckZPjSygO0c>; Jul. 19, 2021.
Diamonox Advanced Diamond Technologies; Ozone Generator G3 Product page; Downloaded Feb. 17, 2020.
Diamonox Advanced Diamond Technologies; Ozone Generator Mini product page; Downloaded Feb. 17, 2020.
Diamonox Advanced Diamond Technologies; Ozone; Product Page; Downloaded Feb. 17, 2020.
Advanced Diamond Technologies, Inc.; UNCD Electrodes; Technical Performance Data.
Robert B Raffa, Joseph V. Pergolizzi, Robert Taylor, Sanjib Choudhuri and Robert Rodenbeck; Scientific Research Publishing—Persistence of Healthcare-Associated (Nosocomial) Infections Due to Inadequate Hand Hygiene: Part 1—Biological and Treatment Factors; Aug. 9, 2018.
Robert B Raffa, Joseph V. Pergolizzi, Robert Taylor, Sanjib Choudhuri and Robert Rodenbeck; Scientific Research Publishing—Persistence of Healthcare-Associated (Nosocomial) Infections Due to Inadequate Hand Hygiene: Part 2—Human Factors; Aug. 10, 2018.
Robert B Raffa, Joseph V. Pergolizzi, Robert Taylor, Sanjib Choudhuri and Robert Rodenbeck; Scientific Research Publishing—Persistence of Healthcare-Associated (Nosocomial) Infections Due to Inadequate Hand Hygiene: Part 3—Application of Human Factors Engineering to an Ozone Hand Sanitizer; Aug. 10, 2018.

\* cited by examiner

HAND SANITIZING AQUEOUS OZONE SPRAY CHAMBER

CROSS-REFERENCE TO RELATED APPLICATION

This is a nonprovisional patent application of U.S. Provisional Patent Application No. 63/056,299, filed Jul. 24, 2020, and titled Aqueous Ozone Sanitizing System; and U.S. Provisional Patent Application No. 63/056,538, filed Jul. 24, 2020, and titled Ozone Generator Cartridge for Ozonating Water; each of which are incorporated herein by reference.

BACKGROUND

The present invention relates to a system for sanitizing with aqueous ozone, and particularly, to the generation and delivery of aqueous ozone in sanitizing devices, including hand sanitizing devices.

Personal hygiene has long been an essential component of infection prevention, particularly hand hygiene. Subsequent to the implementation of soap as an initial hand hygiene solution, many modalities have been developed to maximize antimicrobial efficacy and improve hand hygiene compliance while minimizing skin irritation. However, there has been little regulation of these products until 2017, when the FDA issued a landmark ruling deeming 24 ingredients unsuitable for use in healthcare solutions. The ruling resulted in one solution, triclosan, being pulled from the market for its well-documented role in causing antimicrobial resistance, and deferred ruling on several others, calling for more safety and efficacy data.

Traditional soap, alcohol, chlorhexidine gluconate, povidone iodine, and benzalkonium chloride have all been widely used in healthcare as hand hygiene solutions, with differing levels of efficacy and risk. A review of literature discussing conclusions from many studies makes clear that there is conflicting evidence about the effectiveness of each product. Efficacy as an outcome variable can be assessed in many ways, making it difficult to compare and synthesize outcomes across studies. Researchers report different primary outcomes (colony-forming unit counts vs. infection rates) and use a variety of experimental designs (in vitro, in vivo, artificial contamination, observational, etc.). Additionally, efficacy often depends on the specific virus or bacterium, the length of time spent cleaning, and the cleaning technique (rubbing, scrubbing, etc.). Another factor that impacts efficacy is acquired self-resistance.

Although consensus about efficacy can be difficult, the collective evidence indicates that microbes can generate resistance to some hand hygiene solutions, and some of these solutions may even foster cross-resistance to other antibiotics. Additionally, skin damage or irritation from repeated use is a concern for many hand hygiene solutions. The limited existing evidence demonstrates a need for a future hand hygiene solution that is broadly effective against bacteria and viruses, while also avoiding both skin damage and bacterial resistance.

Ozone ($O_3$) is known to be a highly effective disinfectant. Ozone is produced when water ($H_2O$) or oxygen ($O_2$) is energized, producing monatomic ($O_1$) molecules that collide with oxygen ($O_2$) molecules to form ozone ($O_3$). The third oxygen atom in ozone is loosely bonded and is therefore highly reactive and readily attaches to and oxidizes other molecules. When used to sanitize, exposure to ozone has been demonstrated to be very effective at killing microorganisms, including bacteria, viruses, and spores.

Aqueous ozone, a solution of water ($H_2O$) and ozone ($O_3$), has also been demonstrated to be effective at sanitizing, i.e., killing microorganisms, when applied at a sufficient combination of ozone concentration and exposure time. Example applications for sanitizing using aqueous ozone include hand sanitizing in place of a soap or other disinfectant wash, the clinical treatment of infected tissue, sanitizing food, and sanitizing medical, food processing, and other instruments and work surfaces.

A concern noted regarding the use of ozone for hand and other tissue sanitizing is the potential adverse effect to human or animal cells if applied at too high of an ozone concentration or for an exposure that is too prolonged, e.g., the 'dosage.' It is known that very high doses of ozone can cause lung and other tissue damage. On the other hand, mild to moderate oxidative cell stress caused by low doses of ozone appears to be suggest a therapeutic effect that benefits and aids tissue healing. While it remains unclear how high a level of exposure would lead to unintended cellular damage or clinically relevant skin pathologies, safety warrants using only the ozone dosage required to achieve the desired logarithmic level of reduction of the targeted microorganisms, which is also expected to be also proven to be of little risk and likely therapeutic benefit to human tissue.

Many prior art systems provide aqueous ozone by generating ozone gas from air, which has lower concentrations of oxygen molecules than water, or from liquid oxygen, which is expensive and difficult to handle logistically and in the process. Further, once gaseous ozone is produced, it must be uniformly distributed and dissolve, which is difficult and inefficient, requiring a number of controlled process steps and often producing excess ozone off-gas and non-uniform distribution of dissolved ozone in the water stream. For the smaller scale of a device or other appliance, for example, for a single user, gaseous generation and mixing effective and efficient for an industrial or municipal scale is not practically applied from a cost, technological, or effectiveness perspective.

In light of the need for improved hand hygiene and other sanitizing solutions providing a well-regulated dosage, a high level of assurance must be incorporated into generating and delivering the desired level of aqueous ozone concentration level, complete area coverage, and the desired exposure time effective at killing targeted microorganisms while not inducing undue oxidative stress to the hands (dermis cells) or other tissues being sanitized.

The present disclosure is a result of the recognition of and response to this need for improved generation and delivery systems for aqueous ozone sanitizing, particularly for hand sanitizing.

SUMMARY

The present invention may comprise one or more of the features recited in the attached claims, and/or one or more of the following features and combinations thereof.

An illustrative aqueous ozone sanitizing system for body part, tissue, and instrument sanitizing, including hand rinsing and sanitizing includes a sanitizing chamber, spray devices configured to simultaneously irrigate the entire left and right hand of a user, at least two aqueous ozone generators each fluidly coupled to a subset of the spray devices, and a housing for the sanitizing chamber having an opening for guiding the user's hand orientation and position into the sanitizing chamber.

Embodiments according to the present disclosure advantageous produce aqueous ozone directly by electrolytic action within a water stream, thereby cost and process efficiently and effectively producing uniformly dissolved ozone in water (aqueous ozone) with minimal off-gassing. The embodiments further produce and deliver the aqueous ozone in a small compact space, minimizing ozone decay in application, and maximizing the rinsing and sanitizing effects of both chemical and mechanical action with a high surface area provided by small uniform particles of aqueous ozone with a high spin rate, applied by direct irrigation to the entire surface of the hands, efficiently loosening and lessening the microbe load.

While not limited to this application and concentration or kill rate, embodiments disclosed herein may be used to sanitize a user's hands with a 0.8 ppm concentration of aqueous ozone at a flowrate of about 3.0 gallons per minute for a duration of 7 seconds, which has demonstrated with the illustrative embodiment to have a antimicrobial effect of providing at least a minimum of a 3 log reduction in the broad spectrum of microorganisms that typical sanitization systems kill (for example, Tentative Final Monograph (TFM) 24), including for example, *Clostridioides difficile* (*C. diff*). Additionally, embodiments disclosed herein can provide up to a 4.0 ppm concentration of aqueous ozone over different periods of time and different flowrates to meet the needs of various applications and uses. In some embodiments the sanitizer may be configured and used to operate as a wellness rinse without specific healthcare or medical disinfection performance criteria standards or approvals, and in other embodiments the sanitizer may be configured and used to operate as a medical device in a healthcare environment, including for example, for treatment and/or sterilization, with appropriate governmental and/or industry approvals and performance criteria standards, including, for example, with other body parts, tissue, or objects, including instruments.

An illustrative embodiment of an aqueous ozone sanitizer, comprises a sanitizing chamber for dispensing aqueous ozone onto a user's hands; a left plurality of spray devices coupled to the sanitizing chamber configured to simultaneously irrigate a user's entire left hand positioned within a left spray zone of the chamber, the left plurality of spray devices including at least a first left-upper spray device located above the left spray zone and at least a first left-lower spray device located below the left spray zone; a right plurality of spray devices coupled to the sanitizing chamber configured to simultaneously irrigate a user's entire right hand positioned within a right spray zone of the chamber, the right plurality of spray devices including at least a first right-upper spray device located above the right spray zone and at least a first right-lower spray device located below the right spray zone; at least a first and a second aqueous ozone generator coupled to the sanitizing chamber; and wherein: a first subset of the left plurality of spray devices and the right plurality of spray devices are fluidly couple to the first aqueous ozone generator; a second subset of the left plurality of spray devices and the right plurality of spray devices are fluidly couple to the second aqueous ozone generator; and whereby the position of the first and the second aqueous ozone generators relative to the left and right plurality of spray devices and a selection of the first subset and the second subset minimizes the distance between each of the left and the right plurality of spray devices and the one of the first and the second aqueous ozone generators to which it is fluidly coupled, thereby minimizing a depletion of ozone concentration between the first and the second aqueous ozone generators and the left and the right plurality of spray devices.

Additionally, or alternatively, in any subcombination, wherein: the first aqueous ozone generator is positioned adjacent the left plurality of spray devices; the first subset includes all the left plurality of spray devices; the second aqueous ozone generator is positioned adjacent the right plurality of spray devices; and the second subset includes all the right plurality of spray devices; wherein: the first aqueous ozone generator is positioned adjacent first left-upper spray device and the first right-upper spray device; the first subset includes the first left-upper spray device and the first right-upper spray device; the second aqueous ozone generator is located adjacent first left-lower spray device and the first right-lower spray device; and and the second subset includes the first left-lower spray device and the first right-lower spray device.

Additionally, or alternatively, in any subcombination, further comprising: a housing for the sanitizing chamber defining at least one opening to receive the user's left and right hands; and wherein the housing defines at least one of a horizontal marking feature and a vertical marking feature for each of the user's left and right hands, thereby providing a guide to instruct an insertion point of the user's left and right hands through the at least one opening and into the corresponding ones of the left and the right spray zones; further comprising: a housing for the sanitizing chamber defining a pair of openings to receive each of the user's left and right hands, each of the pair of openings defining an opening vertical span and an opening horizontal span; and wherein the opening vertical span is greater than the opening horizontal span, thereby instructing and guiding the user's hands into a vertical orientation upon insertion through each of the openings; wherein the ratio of the opening horizontal span to the opening vertical span is less than 3:4; wherein the ratio of the opening horizontal span to the opening vertical span is about 2:3; wherein the ratio of the opening horizontal span to the opening vertical span is less than 2:3; wherein the sanitizing chamber housing further defines a channel connecting the pair of openings, the channel defining a channel vertical span smaller than the opening vertical span; wherein the ratio of the channel vertical span to the opening vertical span is less than 3:4; wherein the ratio of the channel vertical span to the opening vertical span is about 2:3; wherein the ratio of the channel vertical span to the opening vertical span is less than 2:3;

Additionally, or alternatively, in any subcombination, wherein the left plurality of spray devices further includes a second left-upper spray device and a second left-lower spray device; and a right plurality of spray devices further includes a second right-upper spray device and a second left-lower spray device; wherein the left spray zone is defined by a bounded area of irrigated space provided by the positions, orientations, and overlapping spray patterns of the left plurality of spray devices; and the right spray zone is defined by a bounded area of irrigated space provided by positions, orientations, and overlapping spray patterns of the right plurality of spray device; wherein the positions, orientations, and overlapping spray patterns of the left plurality of spray devices provide simultaneously irrigation of the entire left hand of the user when oriented with the user's left palm facing the user's right hand; and the positions, orientations, and overlapping spray patterns of the right plurality of spray devices provide simultaneously irrigation of the entire right hand of the user when oriented with the user's right palm facing the user's left hand; wherein each of the left and right spray zone encompasses less than 320 cubic inches; wherein each of the left and right spray zones span between about 3.5 to about 4.5 inches along an anterior-posterior axis, span about 8 inches along an lateral-medial axis, and span about 10 inches along a proximal-distal axis; wherein each of the left and right spray zones define a proximal-distal axis that is oriented to about 15 degrees sloped downwardly in a direction extending from the pair of openings into the sanitizing chamber; wherein each of the left and right spray zones define a lateral-medial axis that is oriented to between about 10 degrees and 25 degrees sloped outwardly in a direction extending from the bottom toward the top of sanitizing chamber; wherein a displacement in angular alignment of a central axis of spray between each of the first upper-right spray device and the second upper-right spray device is between 30 degrees to 50 degrees about each of an anterior-posterior axis and about a proximal-distal axis; wherein a difference in angular alignment of a central axis of spray between each of the first lower-right spray device and the second lower-right spray device is between 0 degrees to 10 degrees about each of an anterior-posterior axis and about a proximal-distal axis; wherein each of the left and each of the right plurality of spray devices each define at least one fluidic oscillator providing a spray pattern for each spray device spanning about 16 degrees about a first axis and spanning about 32 degrees about a second axis which is perpendicular to the first axis.

An alternative embodiment of an aqueous ozone sanitizer, comprises: sanitizing chamber for dispensing aqueous ozone onto a user's hands; a left plurality of spray devices coupled to the sanitizing chamber and located and oriented to simultaneously irrigate a user's entire left hand positioned within a left spray zone of the chamber, the left plurality of spray devices; a right plurality of spray devices coupled to the sanitizing chamber and located and oriented to simultaneously irrigate a user's entire right hand positioned within a right spray zone of the chamber; a first aqueous ozone generator located adjacent to and fluidly coupled to the left plurality of spray devices; a second aqueous ozone generator located adjacent to and fluidly coupled to the right plurality of spray devices; and whereby the position of the first and the second aqueous ozone generators relative to the left and right plurality of spray devices minimizes a depletion of ozone concentration between the first and the second aqueous ozone generators and the left and the right plurality of spray devices.

Additionally or alternatively, in any subcombination, wherein: a first spray device of the left plurality of spray devices is positioned laterally of the left hand and is further positioned and oriented to irrigate a dorsal side of a metacarpal region and phalangeal region of the left hand; a second spray device of the left plurality of spray devices is positioned laterally of the left hand and is further positioned and oriented to irrigate a dorsal side of a phalangeal region of the left hand; a third spray device of the left plurality of spray devices is positioned medially of the left hand and is further positioned and oriented to irrigate an anterior side of the carpus region and the metacarpal region of the left hand; and a fourth spray device of the left plurality of spray devices is positioned medially of the left hand and is further positioned and oriented to irrigate an anterior side of the phalangeal region of the left hand; wherein the fourth spray device of the left plurality of spray devices is further position and oriented to also irrigate an anterior side of the metacarpal region of the left hand; wherein: the first spray device of the left plurality of spray devices is further position and oriented to also irrigate an anterior side of at least one of the metacarpal region and the phalangeal region of the left hand; the third spray device of the left plurality of spray devices is further position and oriented to also irrigate a dorsal side of at least one of the carpus region and the metacarpal region of the left hand; and the fourth spray device of the left plurality of spray devices is further position and oriented to also irrigate a dorsal side of at least one of the phalangeal region of the left hand; wherein the fourth spray device of the left plurality of spray devices is further position and oriented to also irrigate the metacarpal region of the left hand; wherein the left plurality of spray devices further comprises a fifth spray device positioned laterally of the left hand and further positioned and oriented to irrigate an anterior side of the carpus region and the metacarpal region of the left hand.

For purposes of this disclosure, including the claims, the term 'about' is defined as within a definite range of +/−10% of the referenced value. Additional features of the disclosure will become apparent to those skilled in the art upon consideration of the following detailed description of the illustrative embodiment.

BRIEF DESCRIPTION OF THE DRAWINGS

The detailed description particularly refers to the accompanying Figs. in which.

DESCRIPTION OF THE ILLUSTRATIVE EMBODIMENTS

Figure 1A:
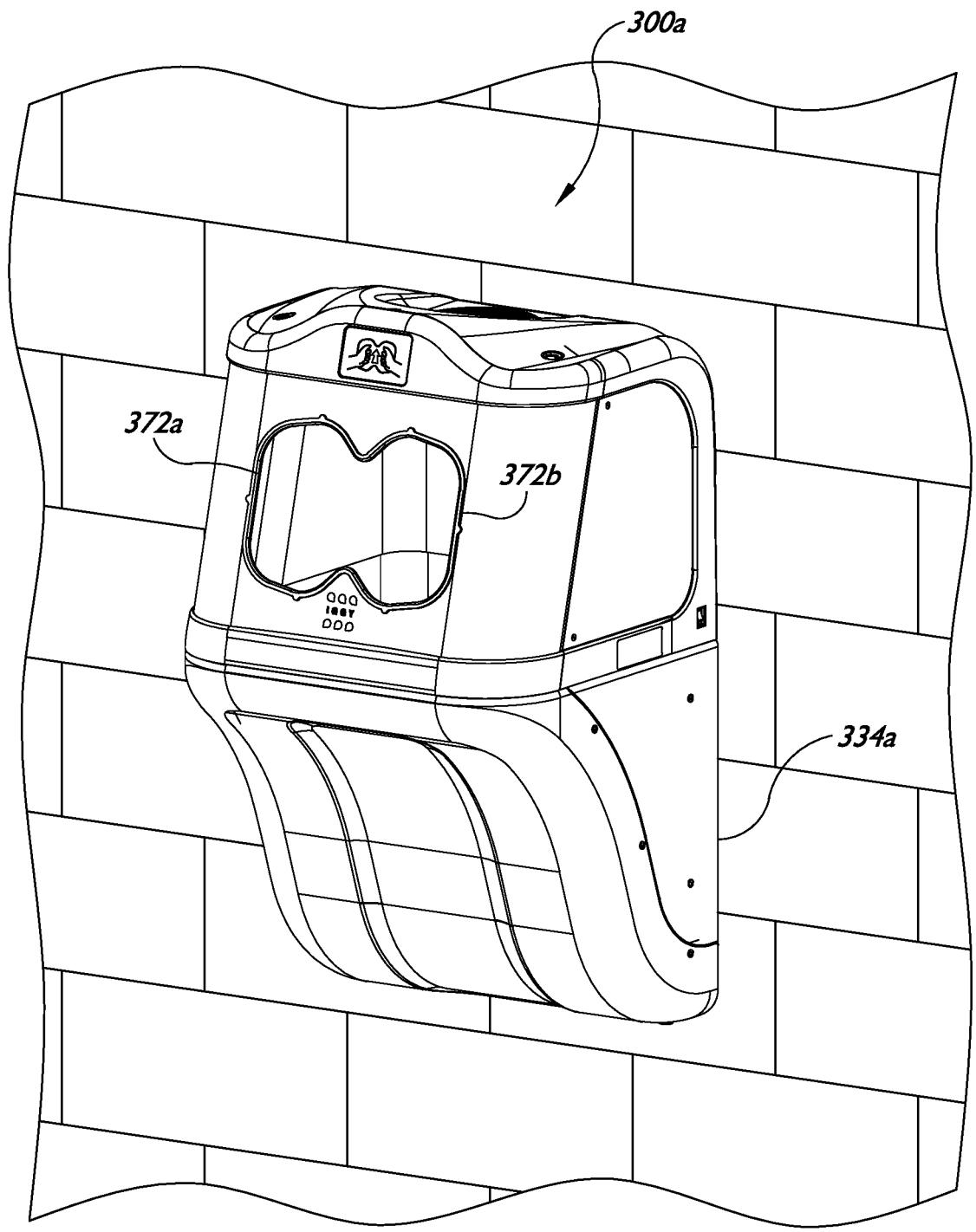
FIG. 1A is a perspective assembly view of a first illustrative embodiment of an aqueous ozone sanitizing system according to the present disclosure.
Figure 1B:
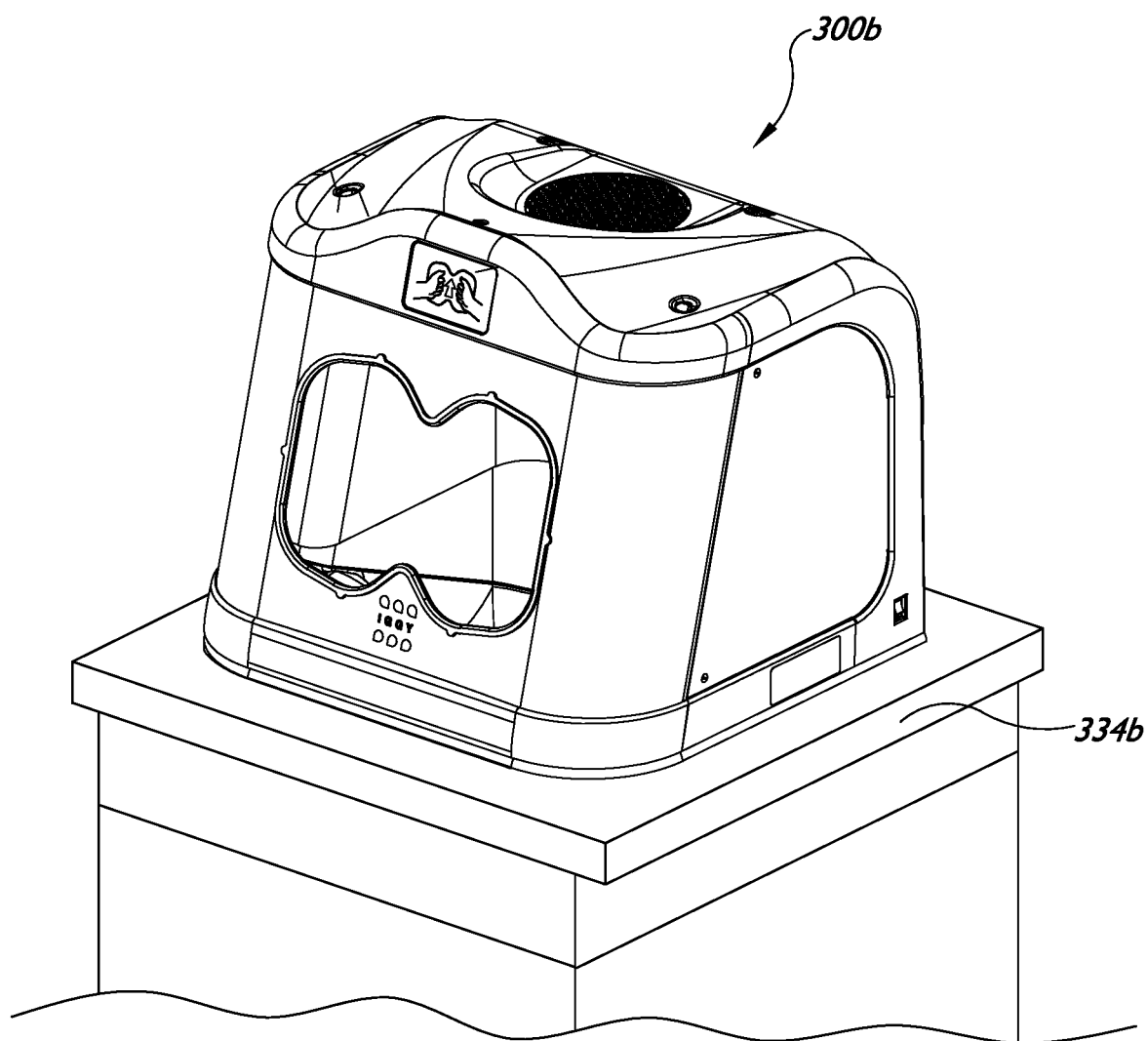
FIG. 1B is a perspective assembly view of a second illustrative embodiment of an aqueous ozone sanitizing system according to the present disclosure.

For the purposes of promoting and understanding the principals of the invention, reference will now be made to one or more illustrative embodiments shown in the drawings and specific language will be used to describe the same.

Overview

Figure 3A:
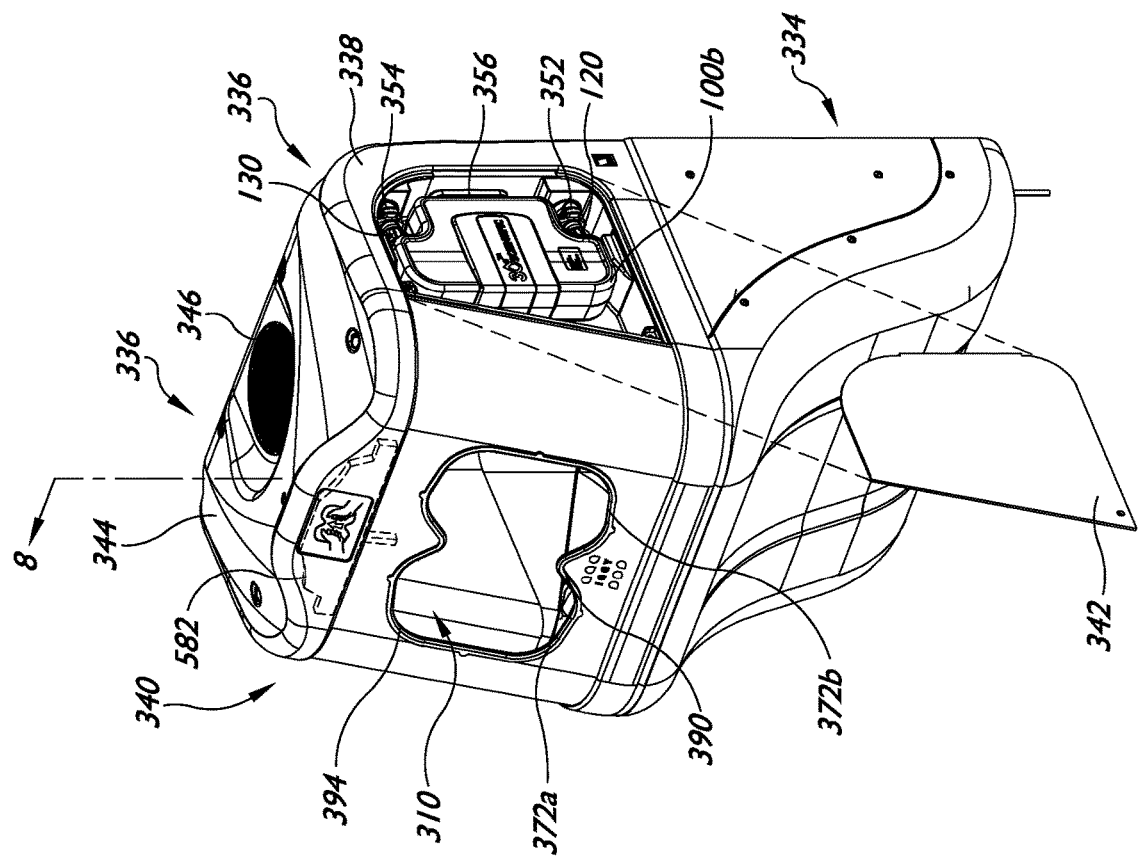
FIG. 3A is front perspective view the aqueous ozone sanitizing system of FIG. 1A.
Figure 2:
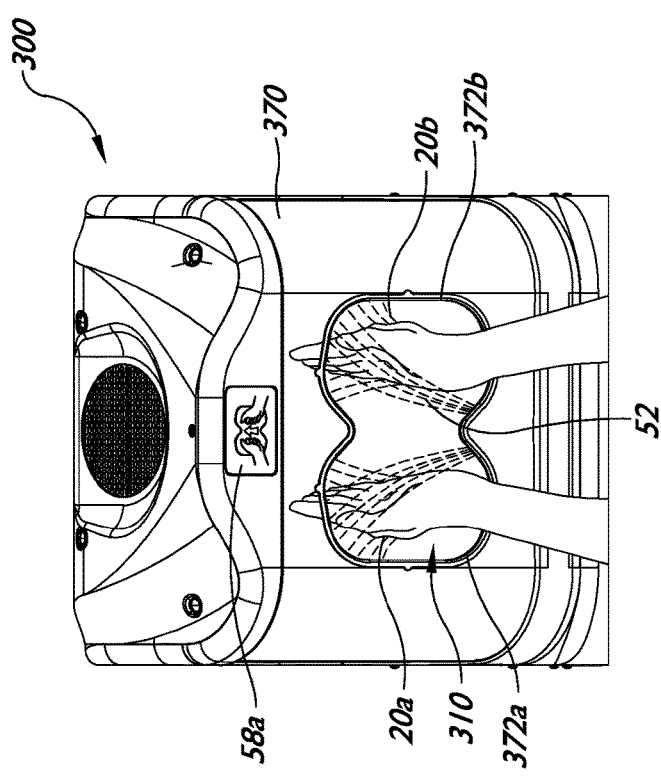
FIG. 2 is a user point of view of the illustrative embodiments of FIGS. 1A and 1B.
Figure 5:
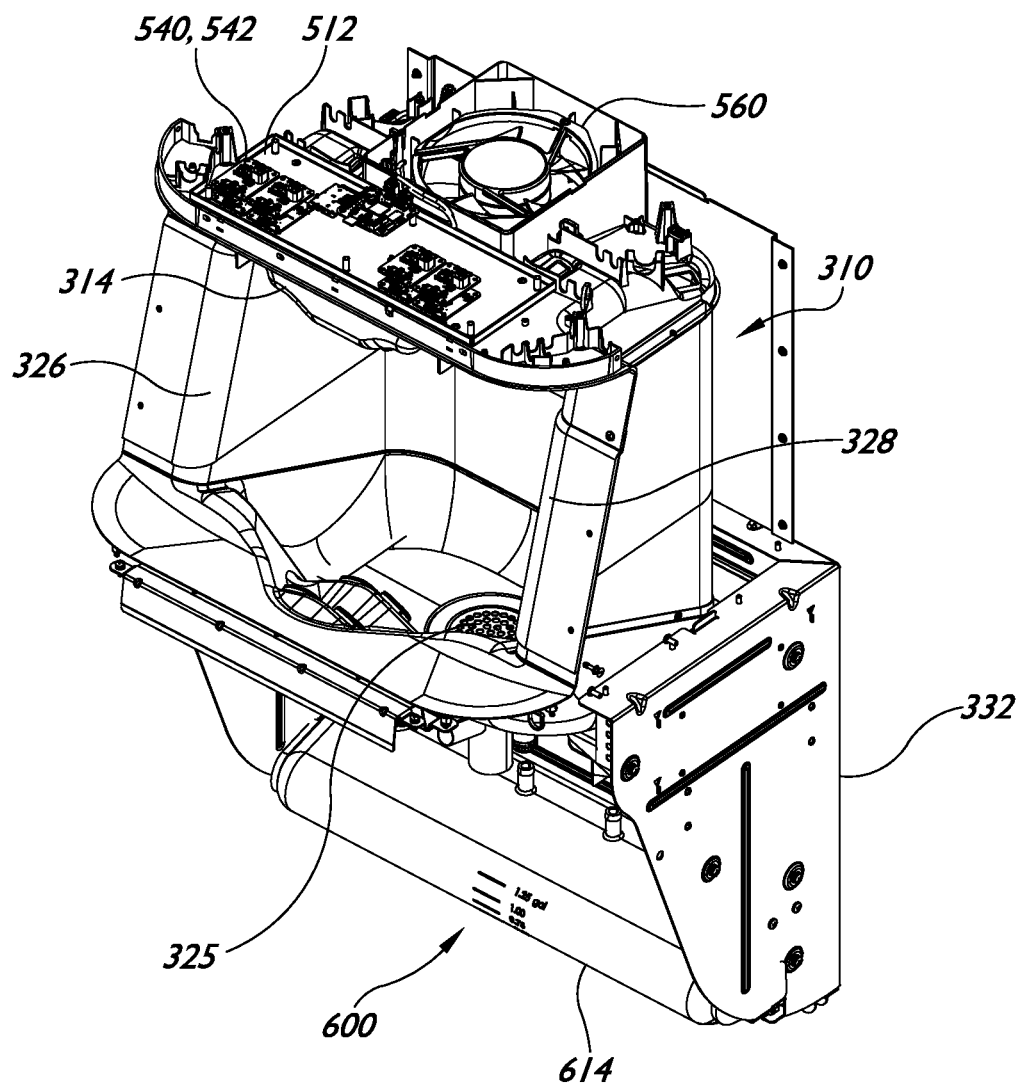
FIG. 5 is a partial perspective assembly view of the aqueous ozone sanitizing system of FIG. 1A.

Referring to FIG. 1A, a first illustrative aqueous ozone sanitizing system for tissue sanitizing, forms a wall mounted hand sanitizer 300a suitable for general commercial or healthcare facility use. A second embodiment forms a counter mount hand sanitizer 300b for like usage, but rather than including lower portion 334a for wall mounting, the counter mount hand sanitizer is configured to provide or mount to an existing countertop 334b or similar horizontal support surface. Referring to FIGS. 2, 3A and 5, the embodiments include a hooded sanitizing chamber 310 defining openings 372a-b for hands 20, spray devices 410 and 430, a docketing receptacle 350 for pluggably receiving a replaceable ozone generator 100, and a controller 512 and hand sensors 590 for sensing hand position and orientation, for delivering a desired ozone concentration and duration, and for tracking usage, including personnel sanitizing practice compliance.

While the illustrative embodiment discusses sanitizing of a user's hands, other embodiments within the scope of the claimed invention include sanitizing systems suitable for sanitizing other body parts, for example, hands and forearms or feet, and for sanitizing other objects, for example, including tools or instruments such as medical devices, so it is under stood that an object or a different body part or tissue can be substituted for all occurrences of the disclosure reciting 'a hand.'

The ozone generator 100 (FIG. 15) used with the hand sanitizer 300 may included more than one ozone generation cells 210a-d. Additionally, quality sensors, for example, including but not limited to sensor determining aqueous ozone concentration, for example oxidation-reduction potential sensors 230 and 240a-b, may optionally be housed within the replaceable ozone generator 100, for example, an untreated water inlet sensor 230 the measurement of which can be used to compare with the measurement of a single or redundant ozonated water outlet sensors 240a-b for controller 512 to determine and control the ozone concentration provided by the generator 100 to a desired level. Sensors may also be included in ozone generator 100 and/or sanitizer 300 that provide measurement of other properties and parameters of water, aqueous ozone, and the components of system 300 include generator 100 discussed here.

Referring to FIG. 2, the front cover 370 defines a left opening 372a is configured to guide a left hand 20a to a proper position and orientation for a left spray zone (also referred to as an application zone) within the spray chamber 310 and a right opening 372b guides a right hand 20b to a proper position and orientation for a right spray zone within the spray chamber 310, both zones ensuring full coverage of hands 20 with the direct spray of ozonated water 52. The user interface 584 may include fixed markings or markings animated by the controller 512, presence sensor 582, and/or hand sensors 590 to further guide timing of insertion, withdrawal, and the position and orientation of the hands 20. The front cover 370 may further define additional features for guidance of hands 20 as will be discussed further below.

Figure 3B:
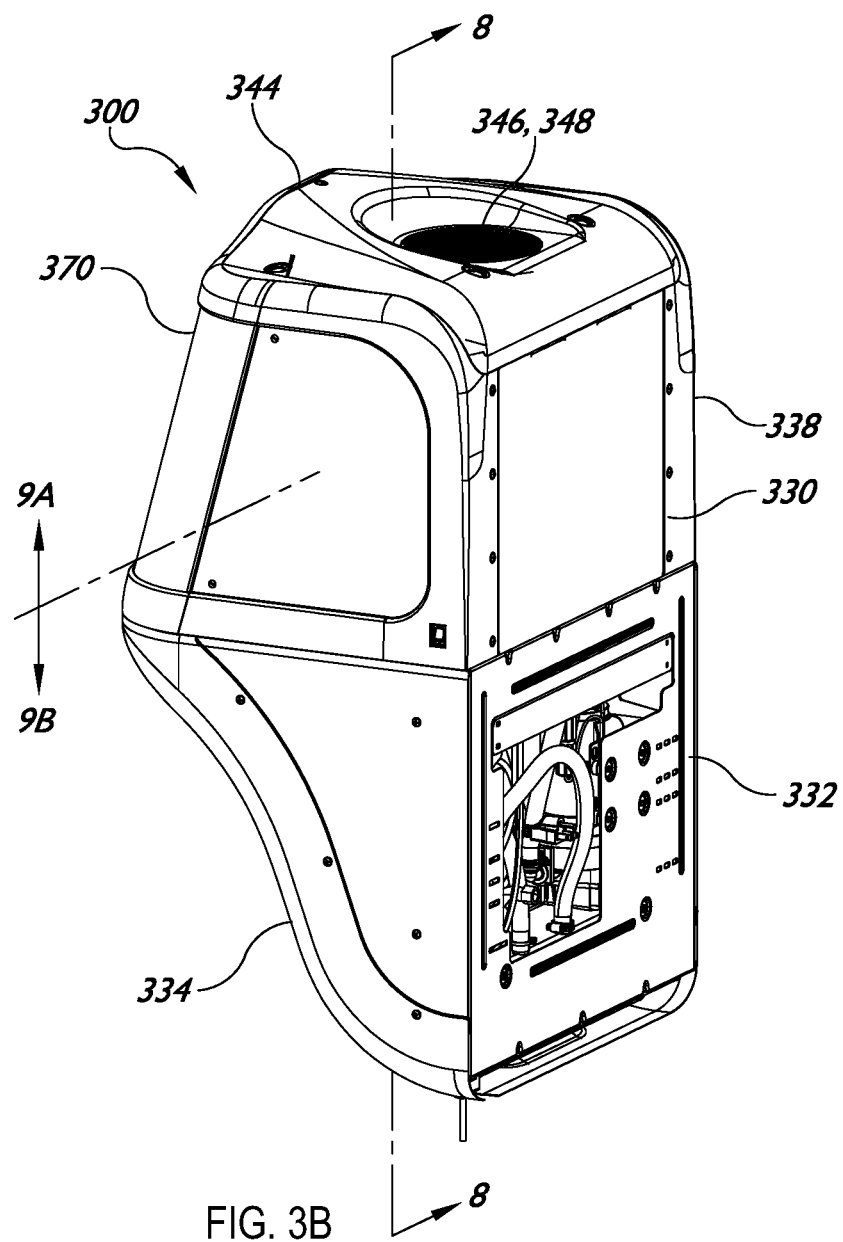
FIG. 3B is rear perspective view the aqueous ozone sanitizing system of FIG. 1A.

Referring to FIGS. 3A and 3B, the hand sanitizer 300 includes a hooded sanitizing chamber 310 and a lower portion 334. The hooding prevents undesirable escape of ozonated water 52 and off-gassed ozone from the chamber 310, and includes covers 336. A top cover 344 includes a fan screen 346 through which air pulled from the chamber 310 and then filtered free of ozone is exhausted. A cover frame 338 includes accessible or removable right cover 342 and left cover 340.

The applicant has found it advantageous to maintaining ozone concentration provided by aqueous ozone generators 100a-b to locate the generators in close proximity to the sanitizing chamber. For example, in at least one embodiment less than a 30% loss of ozone concentration was noted between the aqueous ozone generators 100a-b and the spray chamber 310, therefore, minimizing losses, and controlling the ozone production to account for losses is required.

Opening the covers 340 and 342 provides access to docking receptacle 350a-b in which aqueous ozone generators 100a-b are plugged and are unplugged from and swapped when exhausted, as will be discussed further below. The docking receptacles 350a and 350b provide various water and/or electrical connections to connect the generators 100a-b with other portions of the hand sanitizer as is further described below. Docking receptacles 350a-b are each defined by the housing chassis 330 between each of the left side 326 and right side 328 of the sanitizing chamber 310 and the respective left cover 340 and right cover 342. Some embodiments may include one and some other embodiments more than two docketing receptacles 350a-b to support a different number of simultaneously operated or reserve generators 100a-b.

A control system 500 of the hand sanitizer 300 may include a presence sensor 582 for detection of a user, the function of which will be further described below. The presence sensor 582 may be located with the front cover 370, the adjacent frame 338 above or below the cover, the top cover 344, or the lower portion 334.

Figure 6B:
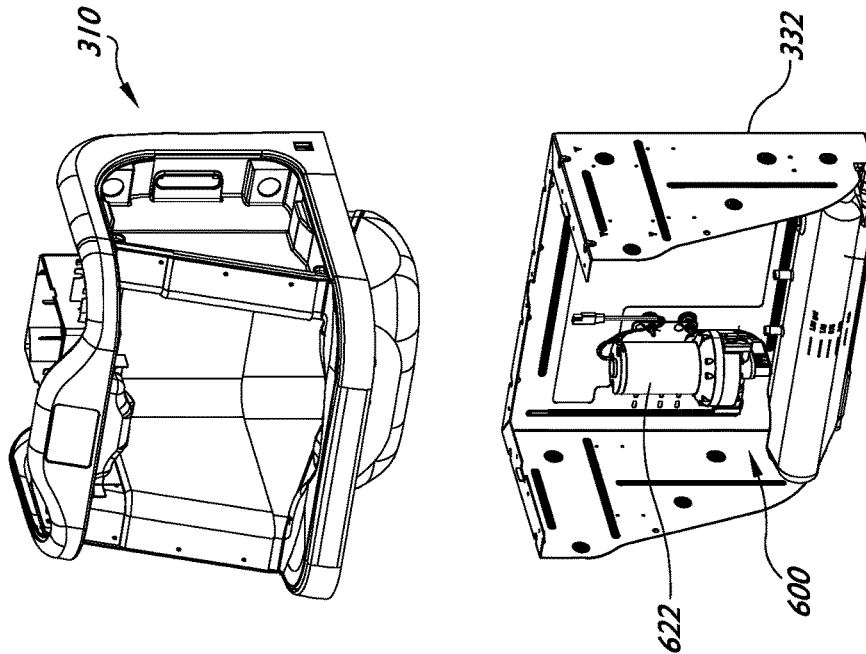
FIG. 6B is an exploded perspective view of a hood portion and lower frame portion of the aqueous ozone sanitizing system of FIG. 1A.
Figure 6A:
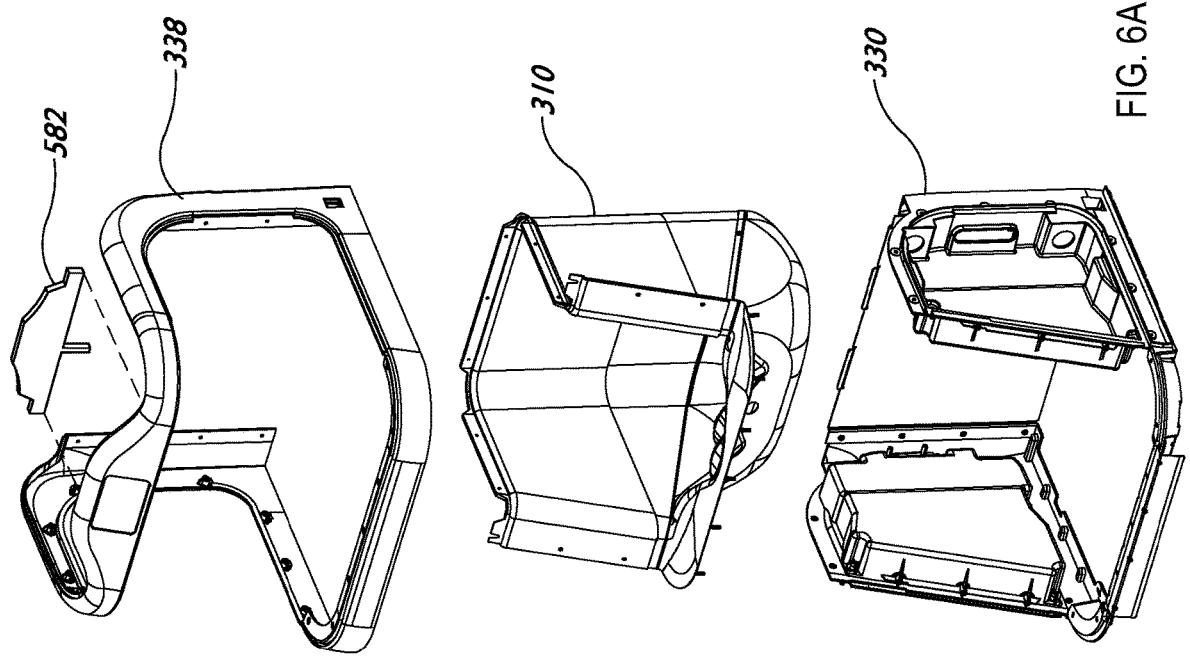
FIG. 6A is an exploded perspective view of a hood portion of the aqueous ozone sanitizing system of FIG. 1A.

The sanitizing chamber 310 and associated cover frame 338 may be coupled to a housing chassis 330, also shown in FIGS. 6A and 6B. The lower frame 332 may be used to attach the hand sanitizer 300 to a wall or other fixed or movable structure, and may also support the chassis 330. Advantageously, the illustrative embodiment of hand sanitizers 300a-b have a sanitizing chamber 310 and cover 336 spanning only about 17.4 inches in height, about 20.5 inches in width, and about 18.6 inches in depth. The lower portion 334 included with sanitizer 300a adds about 19.6 inches in height below the cover 336. The compact size of the hand sanitizers 300a-b is advantageous to the small spaces in commercial or healthcare facilities available for the installation, including as a replacement to traditional handwashing sinks and other sanitizing stations.

Referring to FIGS. 5 and 6B, the lower frame 332 may house portions of the control system 500 and a water supply system 600, including, for example, a power supply 510, an untreated water holding tank 614, a water pump 622, a water filter, and connections to an untreated water supply 50. Other portions of the control system 500 and water supply system 600 may be located between the chamber 310 and the cover frame 338 and associated covers. For example, the controller 512 and associated ozone generator circuits 40, which may be separate from or integral with the controller, may be located between a chamber top 314 and the top cover 344. Additionally, an ozone filter 348 and a fan 560 may be located between the chamber top 314 and the fan screen 346.

Figure 4:
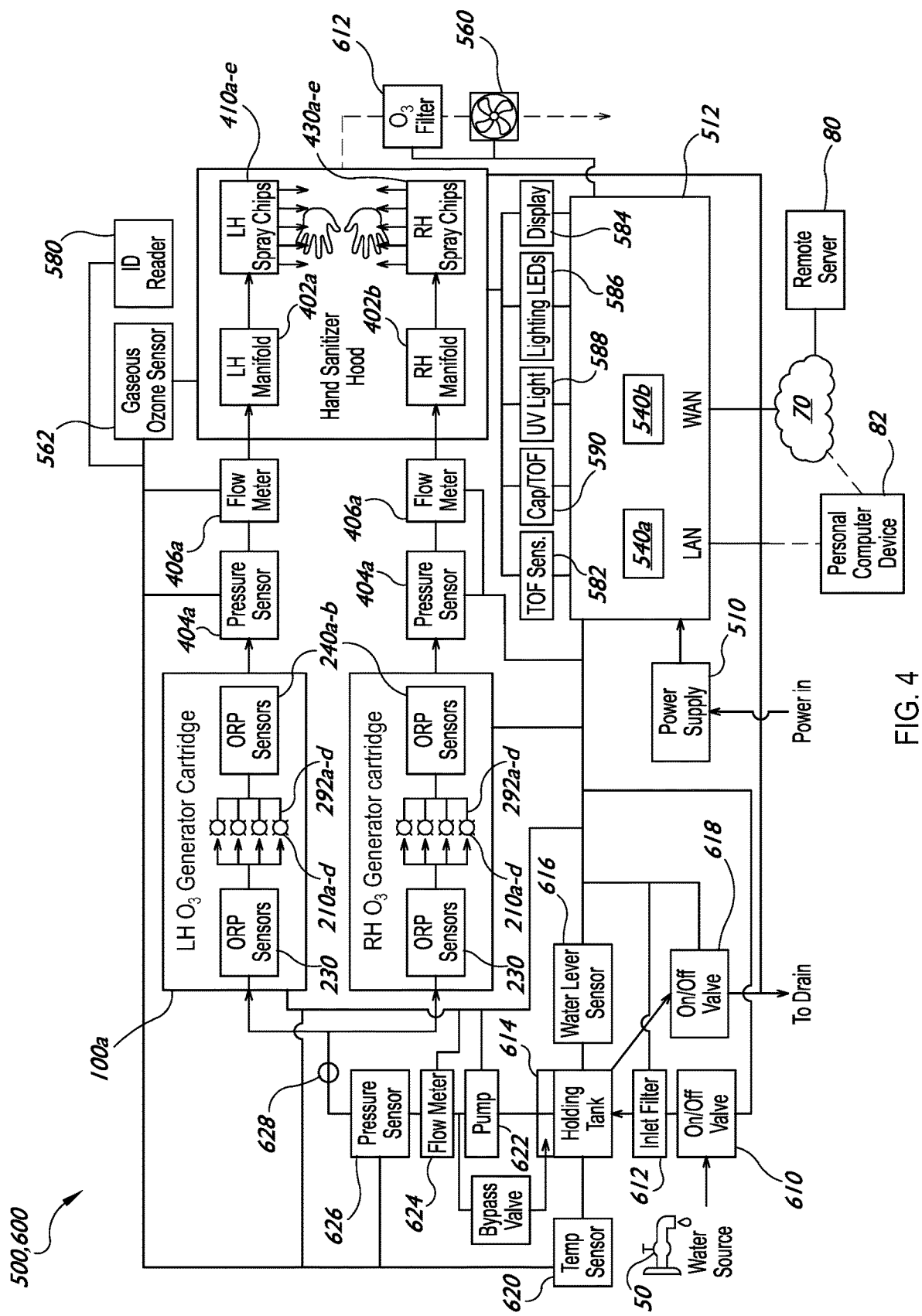
FIG. 4 is an electrical and fluid schematic block diagram of an illustrative embodiment of an aqueous ozone sanitizing system according to the present disclosure.

As illustrated in various cross-sectional views FIGS. 8 and 9A through 10B, A spray system 400 associated with and the sanitizing chamber 310 includes spray devices 410a-e and 440a-e which receive ozonated water 52 from the generators 100a-b and may also include distribution manifolds 402a-b (FIG. 4). The spray devices 410 and 440 are distributed within the sanitizing chamber 310, for example, within a chamber upper half 312, for example, with a chamber top 314, and within a chamber lower half 320, for example, with a chamber bottom 322. The chamber top 314 may include contours 316 that can provide mounting locations for the desired position and/or orientation of the spray devices 410a-c and 430d-e as will be discussed further below. Similarly, the chamber bottom 322a may include contours 324 for spray devices 410d-e and 430d-e. A drain 325 provides an escape path for the spent ozonated water 52 delivered by the spray devices 410a-e and 430a-e, for example, defined through a portion of the chamber bottom 322.

Hood/Chamber Opening

While prior art system are directed to devices that require the rubbing of hands under a unitary stream of aqueous ozone, or hold hands horizontal, palms down as they are sprayed by an oscillating spray bar, at least one of the illustrative embodiments herein uses the increased efficiency and effectiveness offered by position hands so that palms are vertical, facing each other. This position of the hands provides a system 300 having more compact chamber 310, spray zones 420 and 440, reduced distance from aqueous ozone generators 100 to spray zones 420 and 440, an easier position to hold hands in for the user, reduced splashing of water and off-gassed ozone outside of the chamber 310, and longer run-off paths for additional chemical and mechanical action by the aqueous ozone.

Figure 6C:
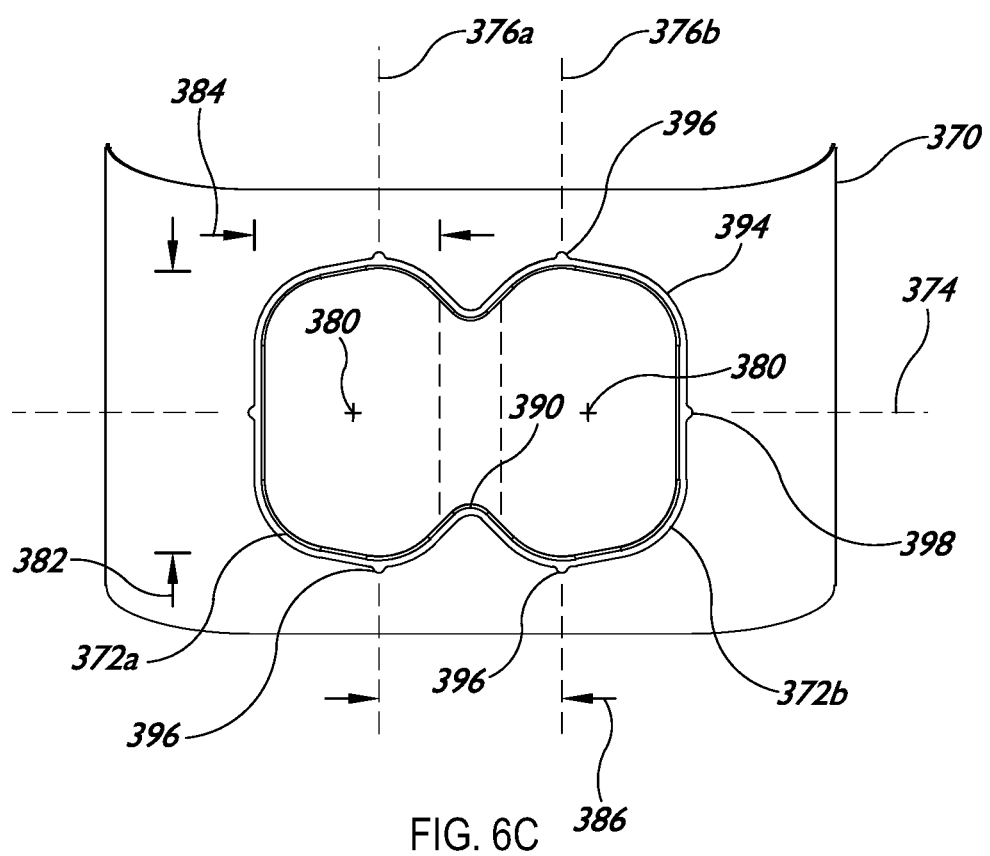
FIG. 6C is a front view of a front hood cover portion illustrating the hand openings of the aqueous ozone sanitizing system of FIG. 1A.

Referring to FIG. 6C, each opening 372a-b of the front cover 370 defines an oblong shape, for example, a stadium as shown in the illustrative embodiment, or an oval, ellipse, or rectangle. The major axis 376a and 376b is oriented perpendicular relative to the floor or ground plane, thereby instructing a vertical orientation for each hand 20 for insertion through the opening, i.e. the palm 34 is oriented perpendicular or closer to perpendicular than horizontal relative to the floor as illustrated in FIG. 2, making it easier to insert each hand while clearing the rim of the opening. The major axes 376a-b of each opening 372a-b defines an opening vertical span 382 from edge to edge of about 8.4 inches and a minor axis 374 defines an opening horizontal span 384 of each opening from edge to edge of about 5.8 inches, providing a ratio of the horizontal span to the vertical span of less than 3:4, additionally or alternatively, about 2:3, and additionally or alternatively, less than 2:3. The distance between centers 380 of the two openings for the illustrative embodiment is about 5.3 inches. These ratios have been discovered to provide visual cues to the user to orient their hands in a palm-to-palm orientation to ensure complete coverage from the ozonated water spray for most efficient sanitization. They also have been discovered to enable minimizing the written or other instructions required by increasing the obviousness of the use and interaction with the sanitizer 300.

In the illustrative embodiment of the sanitizer 300, a channel 390 portion of the area of the between the two openings 372a-b is also opened, thereby connecting the two openings, but retaining enough of the oblong shape of each individual opening 372a-b to retain the overall appearance of a vertical orientation of each opening, thereby retaining the feature instructing a vertical orientation for each hand 20 for insertion through the openings. For example, in the illustrative embodiment, the narrowest vertical span 392 of the channel 390 connecting the two openings 372a-b spans about 5.4 inches, providing a ratio of the opening vertical span (major axis) 382 of each individual opening (8.4 inches) to the vertical span 392 of the connecting channel of less than 3:4, additionally or alternatively, a ratio of about 2:3, and additionally or alternatively, a ratio of less than 2:3.

Defining an open but narrowed channel 390 between the pair of openings 372a-b also provides an advantages to the user of having better visibility of both hands 20 when inserted through the openings and into the chamber 310, retaining the advantage of the channel between the pair of openings be a smaller vertical span than the openings so as to limit the escape of aqueous ozone or ozone off-gas, and guiding the left and right hands 20 to the center 380 of each opening 372a-b. Such advantages are advantageous over prior art openings forming a single horizontal elongate opening of uniform vertical height.

The space between the opening 372a-b that forms the channel 390 is less than 1 inches wide along a horizontal axis 374, thereby the connected pair of openings and channel forming an open horizontal span of about 12 inches. A perimeter formed by the openings 372a-b and channel 390 may include a rim 394 to frame the opening, enhancing one or more of the visual contrast, material properties, or hand edge protection. For example, the rim 394 may be formed from liquid silicone rubber (LSR) or a thermoplastic elastomer (TPE). The front cover 370 may be formed from polyphenylene sulfide (PPS), polyvinylchloride (PVC) and may optionally be translucent or transparent.

The front cover 370 and/or rim 390 may include formed or applied features such as markings 396 and 398 that further guide the position and orientation of the hands as they are inserted through the openings 372a-b and into a static position and orientation within the sanitizing chamber 310. For example, features 398 can provide a vertical position and/or rotational orientation of the hands 20 and features 396 can provide a horizontal position and/or rotational orientation of the hands 20.

The sanitizing chamber 310 and other components in contact with the ozonated water 52 may be constructed from materials resistant to degradation from aqueous ozone, for example, molded from polyphenylene sulfide (PPS). Other portions of the cover 336, frame 338, and lower portion 334 can be constructed from durable materials such as polybutylene terephthalate (PBT), aluminum, stainless steel, and powder-coated steel.

Spray System

At least one prior art device for aqueous ozone hand sanitizing teaches proper sanitization requires hand washing movement, e.g. rubbing or scrubbing of hands together, throughout the aqueous ozone wash cycle. A prior art device also teaches hands held static during the aqueous ozone wash cycle with spray devices located above and below hands orientated horizontally, i.e. palm 34 and dorsal sides 36 parallel to the floor.

In contrast, it has been discovered by the applicant of the instant disclosure that it is advantageous for static hand sanitizing to orient the hands 20 vertically, i.e. thumbs 40 superior (at top) and palms 34 facing each other, in order to achieve a reduction in size of the aqueous ozone hand sanitizer 300, particularly the size of the sanitizing chamber 310 and associated spray system 400, and to minimize the number of spray heads 410 and 430 and maximize the coverage of all regions of the hand 20 with ozonated water 52 with streams directly from the spray devices, i.e., direct irrigation rather than coverage from run-off.

Figure 7A:
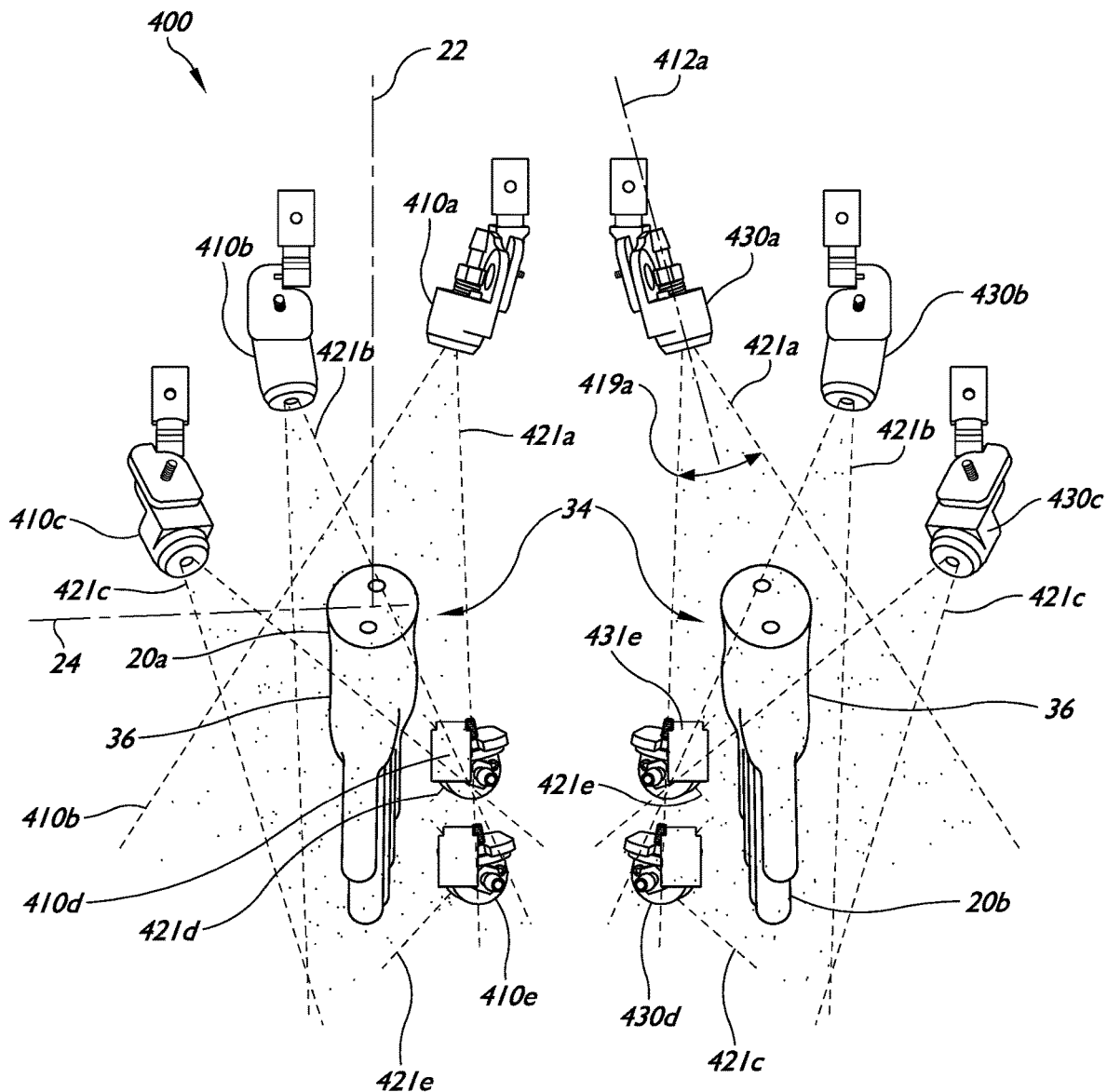
FIG. 7A is a front view illustrating the aqueous ozone spray patterns of a first illustrative embodiment of an aqueous ozone sanitizing system according to the present disclosure.
Figure 7B:
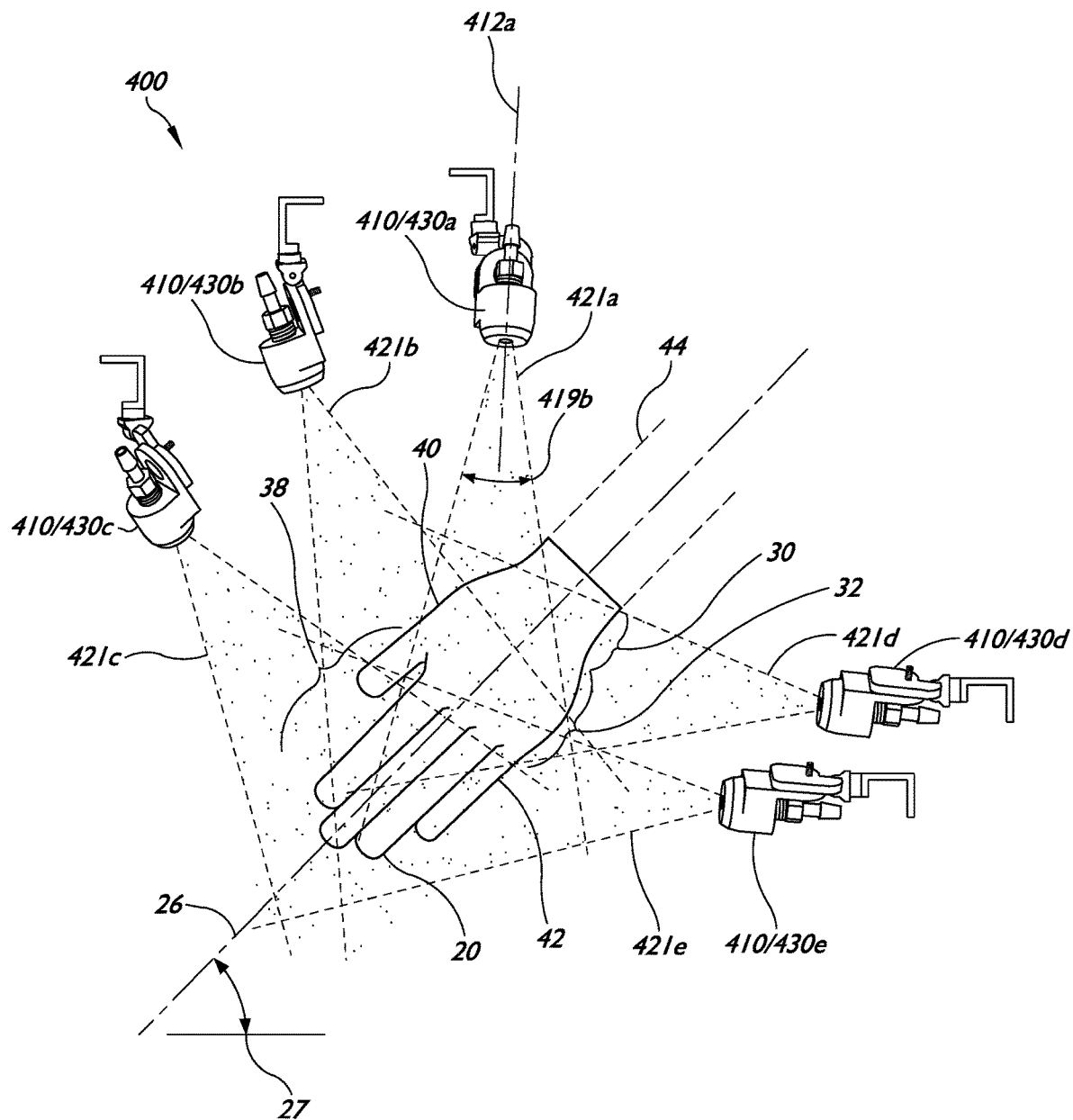
FIG. 7B is a left side view illustrating the aqueous ozone spray patterns of the illustrative embodiment shown in FIG. 7A.
Figure 7C:
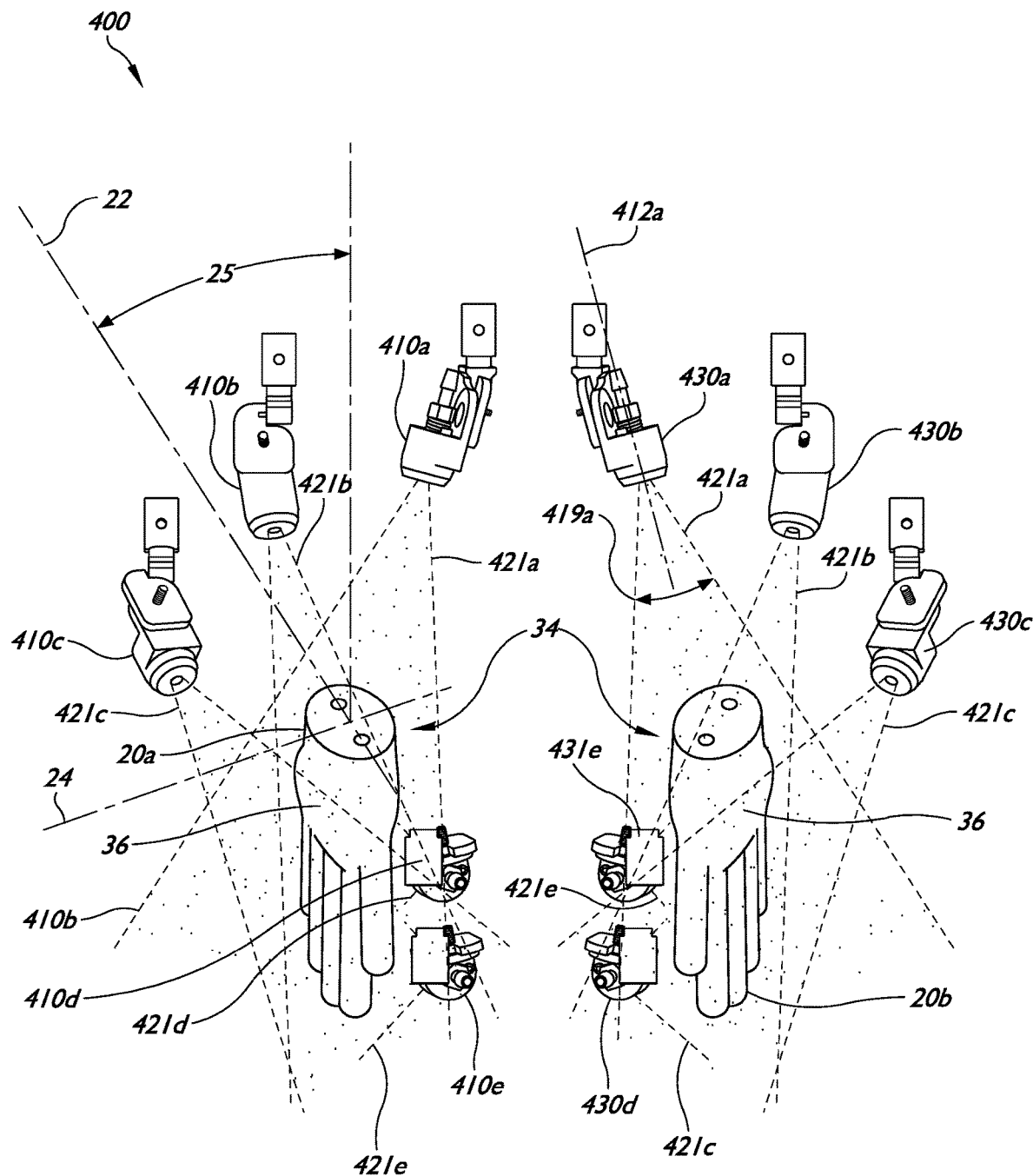
FIG. 7C is a front view illustrating the aqueous ozone spray patterns of a second illustrative embodiment of an aqueous ozone sanitizing system according to the present disclosure.
Figure 8:
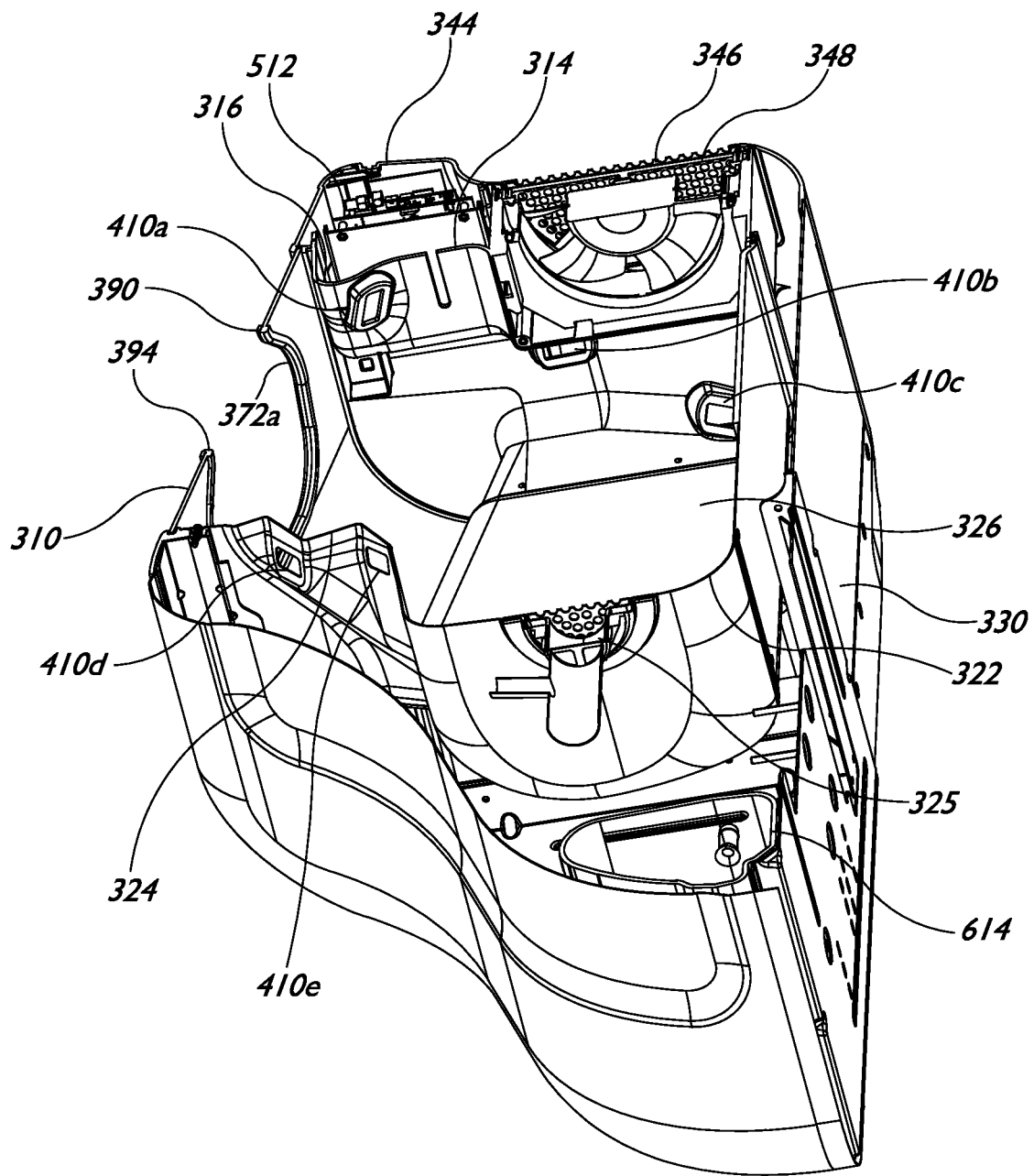
FIG. 8 is a cross-sectional perspective assembly view showing the spray chamber portion of the illustrative embodiment of the aqueous ozone sanitizing system of FIGS. 3A and 3B taken along cutting plane line 8-8 shown in FIG. 3B.
Figure 9B:
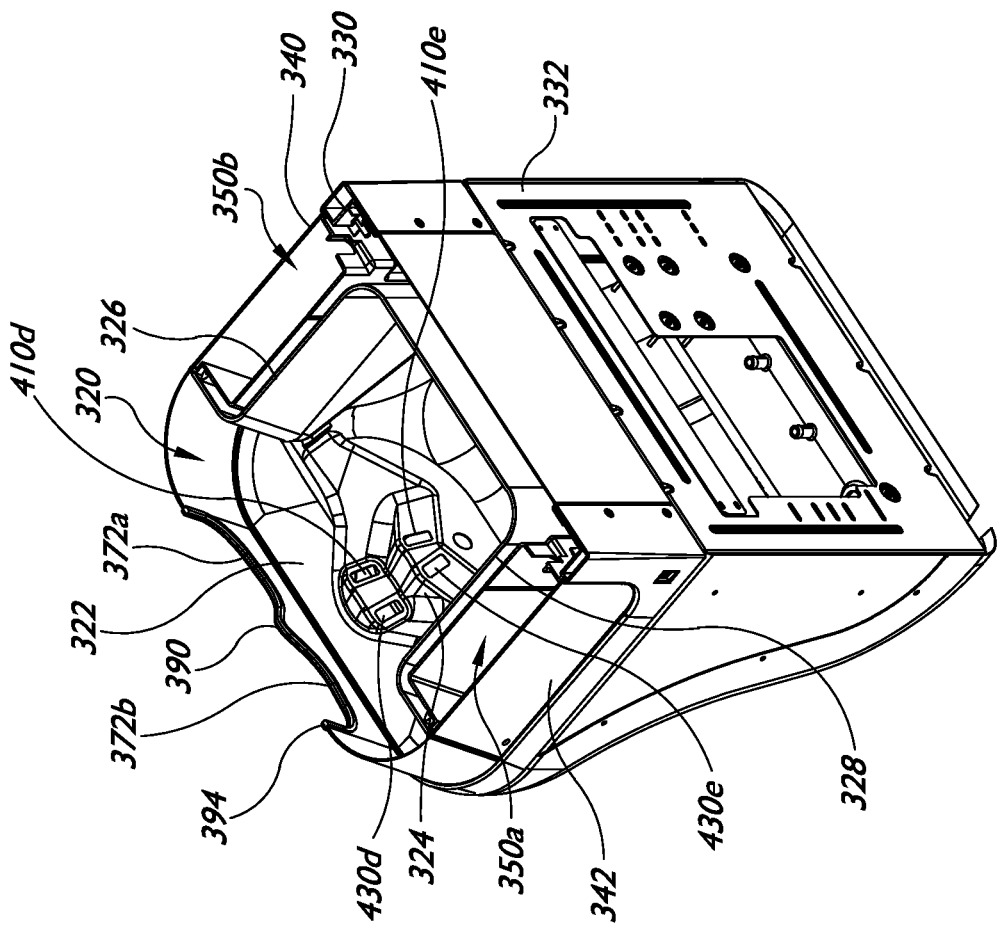
FIG. 9B is a cross-sectional perspective view showing the lower portion of the spray chamber of the illustrative embodiment of the aqueous ozone sanitizing system of FIGS. 3A and 3B taken along cutting plane line 9B-9B shown in FIG. 3B.
Figure 9A:
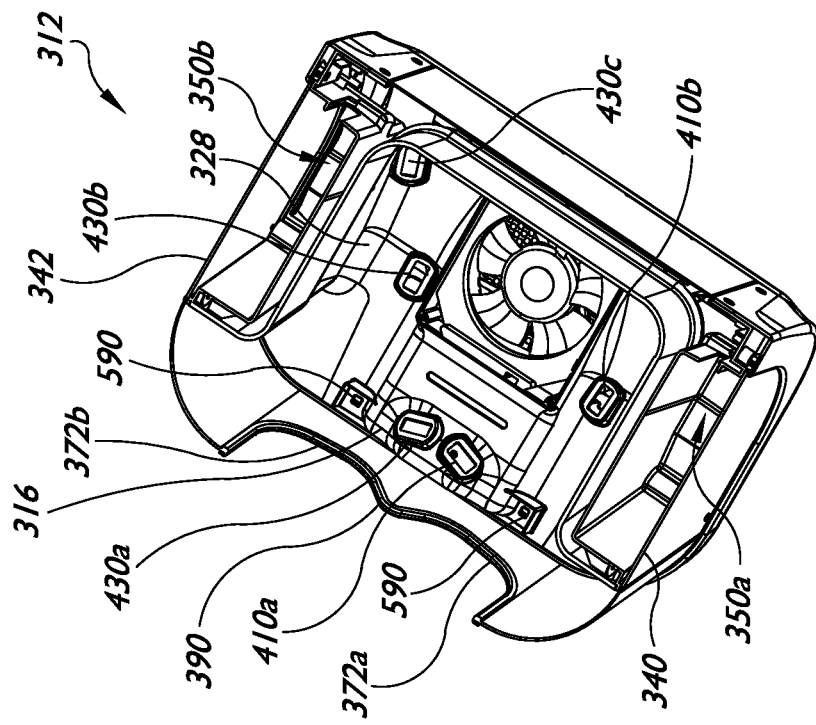
FIG. 9A is a cross-sectional perspective view showing the upper portion of the spray chamber of the illustrative embodiment of the aqueous ozone sanitizing system of FIGS. 3A and 3B taken along cutting plane line 9A-9A shown in FIG. 3B.
Figure 10A:
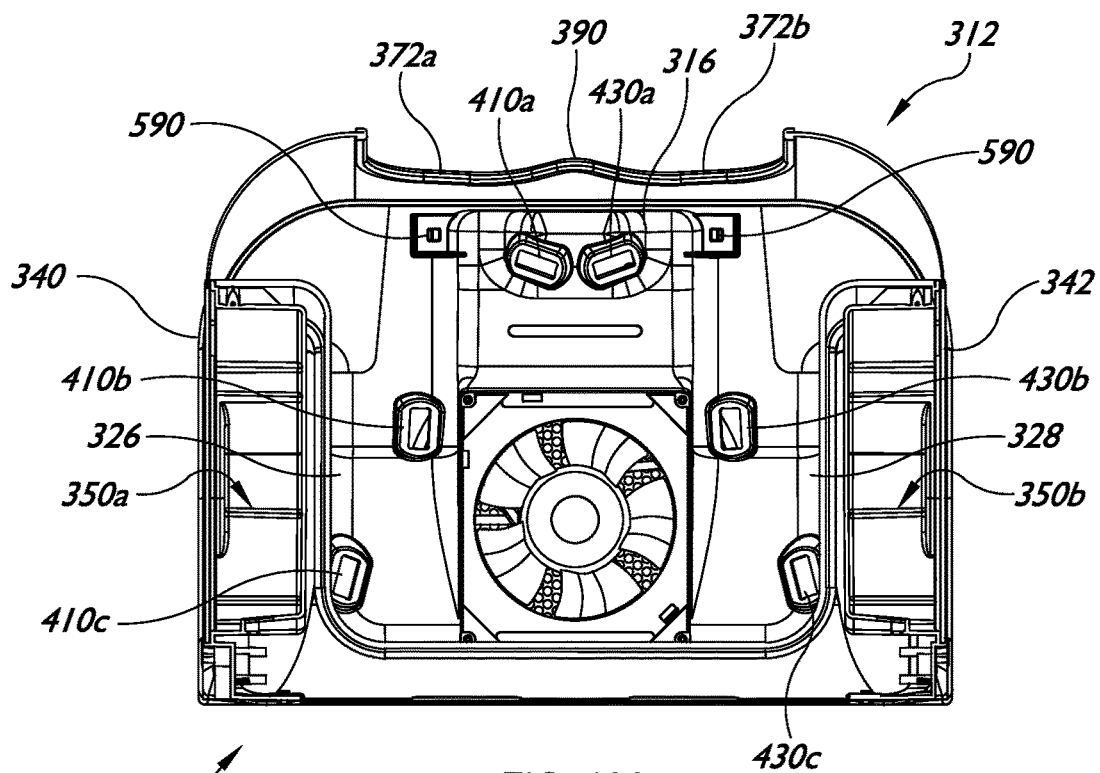
FIG. 10A is a cross-sectional bottom view showing the upper portion of the spray chamber of the illustrative embodiment of the aqueous ozone sanitizing system of FIGS. 3A and 3B taken along cutting plane line 9A-9A shown in FIG. 3B.
Figure 10B:
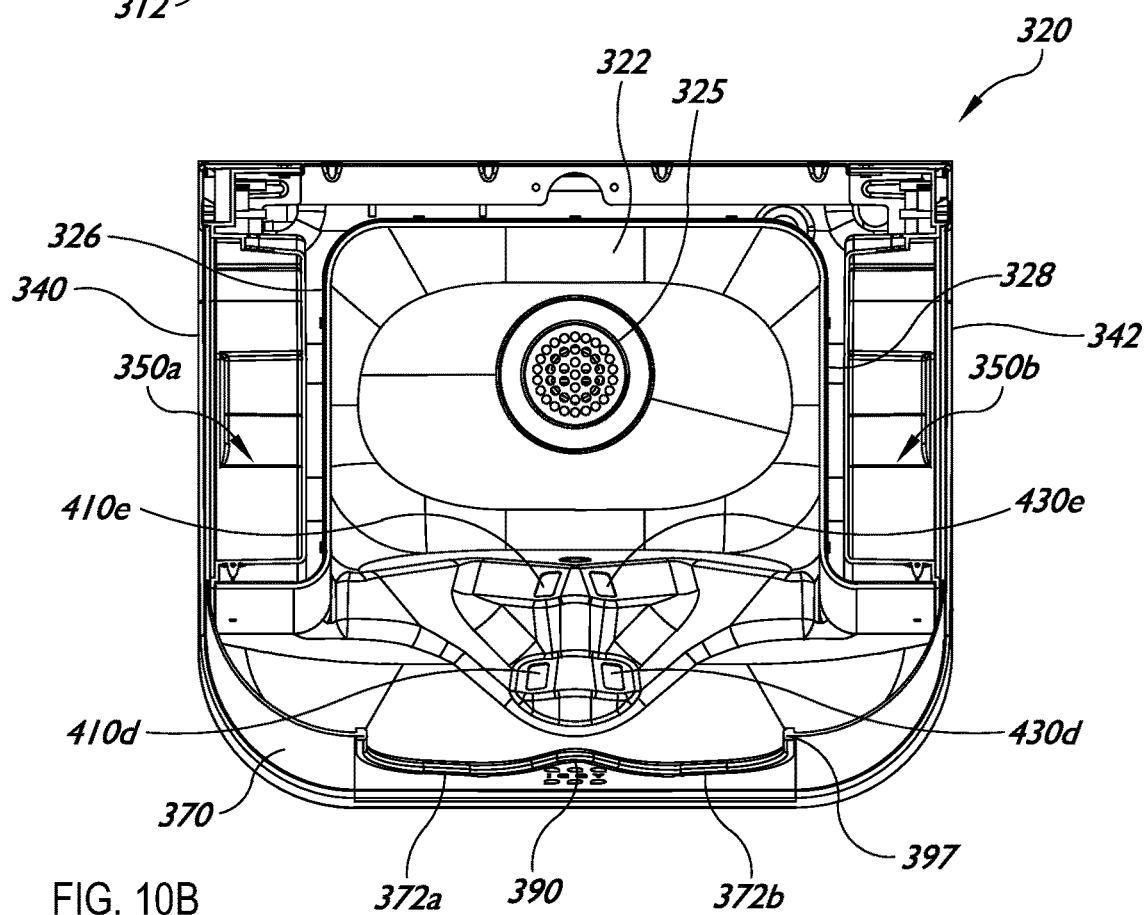
FIG. 10B is a cross-sectional top view showing the lower portion of the spray chamber of the illustrative embodiment of the aqueous ozone sanitizing system of FIGS. 3A and 3B taken along cutting plane line 9B-9B shown in FIG. 3B.
Figure 11A:
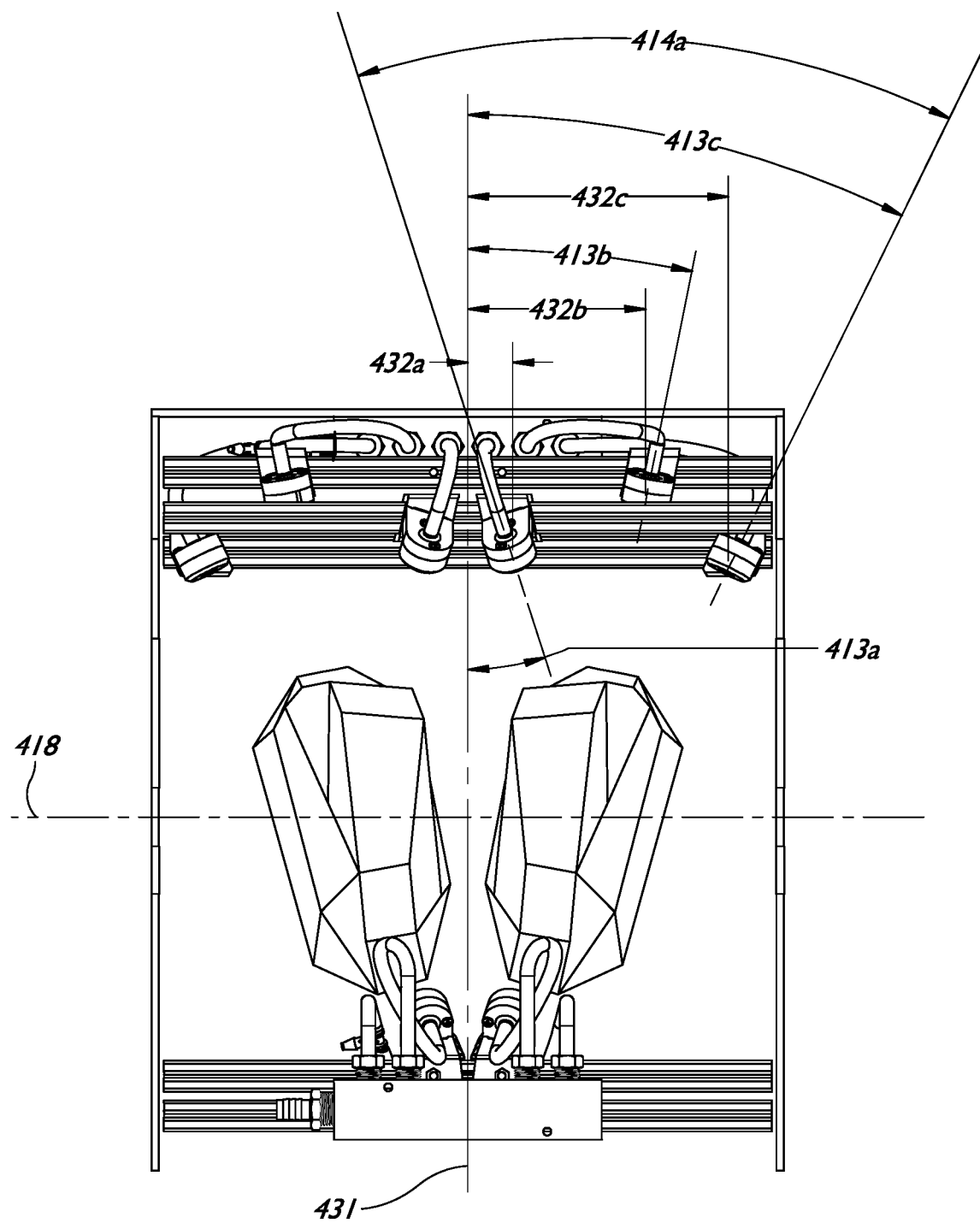
FIGS. 11A and 12A illustrate spray zones and spray devices in a front view of a spray chamber portion of an illustrative embodiment of an aqueous ozone sanitizing system according to the present disclosure.
Figure 11B:
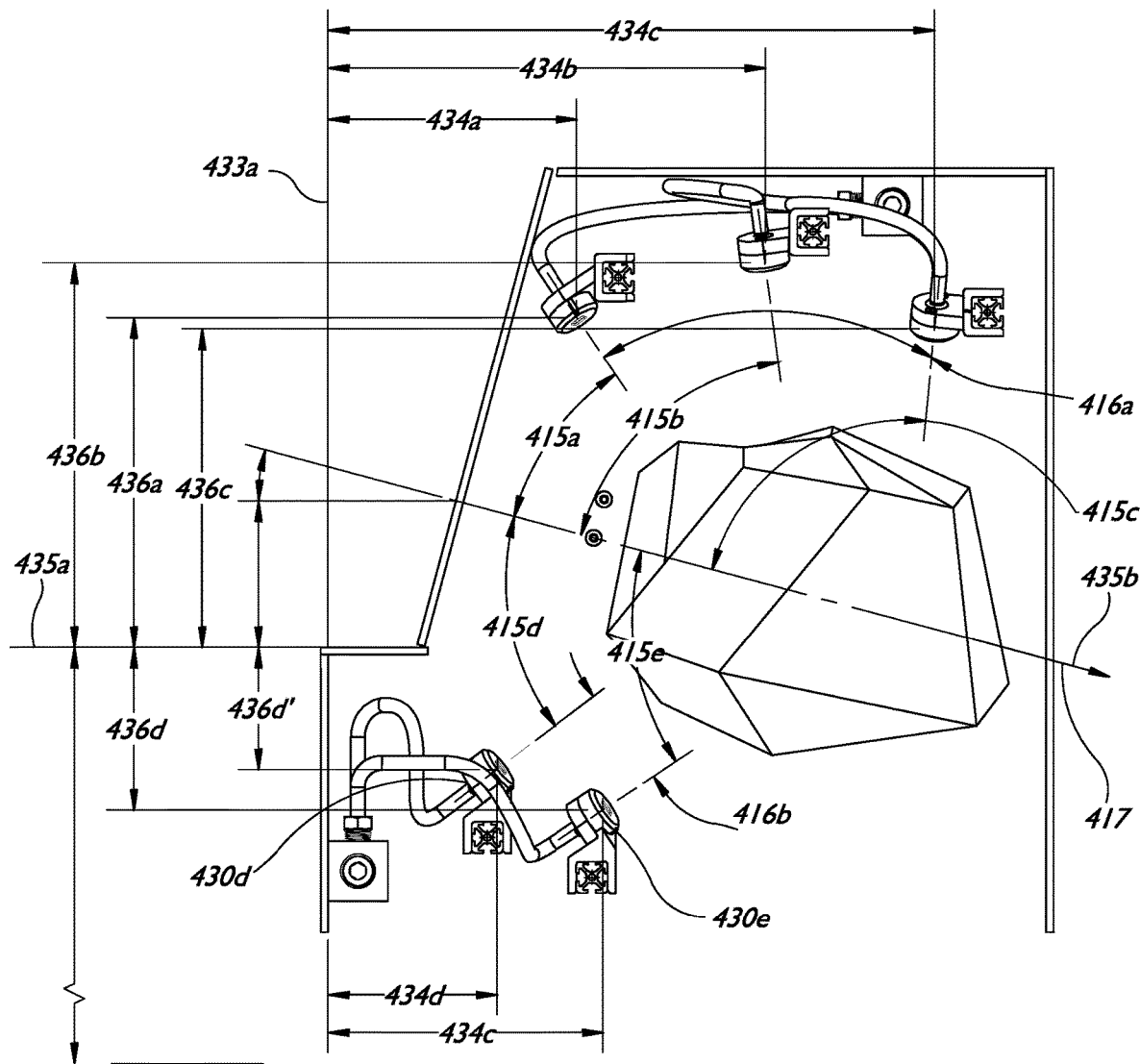
FIGS. 11B and 12B illustrate spray zones and spray devices in a right side view of a spray chamber of the illustrative embodiment of FIGS. 11A and 12A.
Figure 11C:
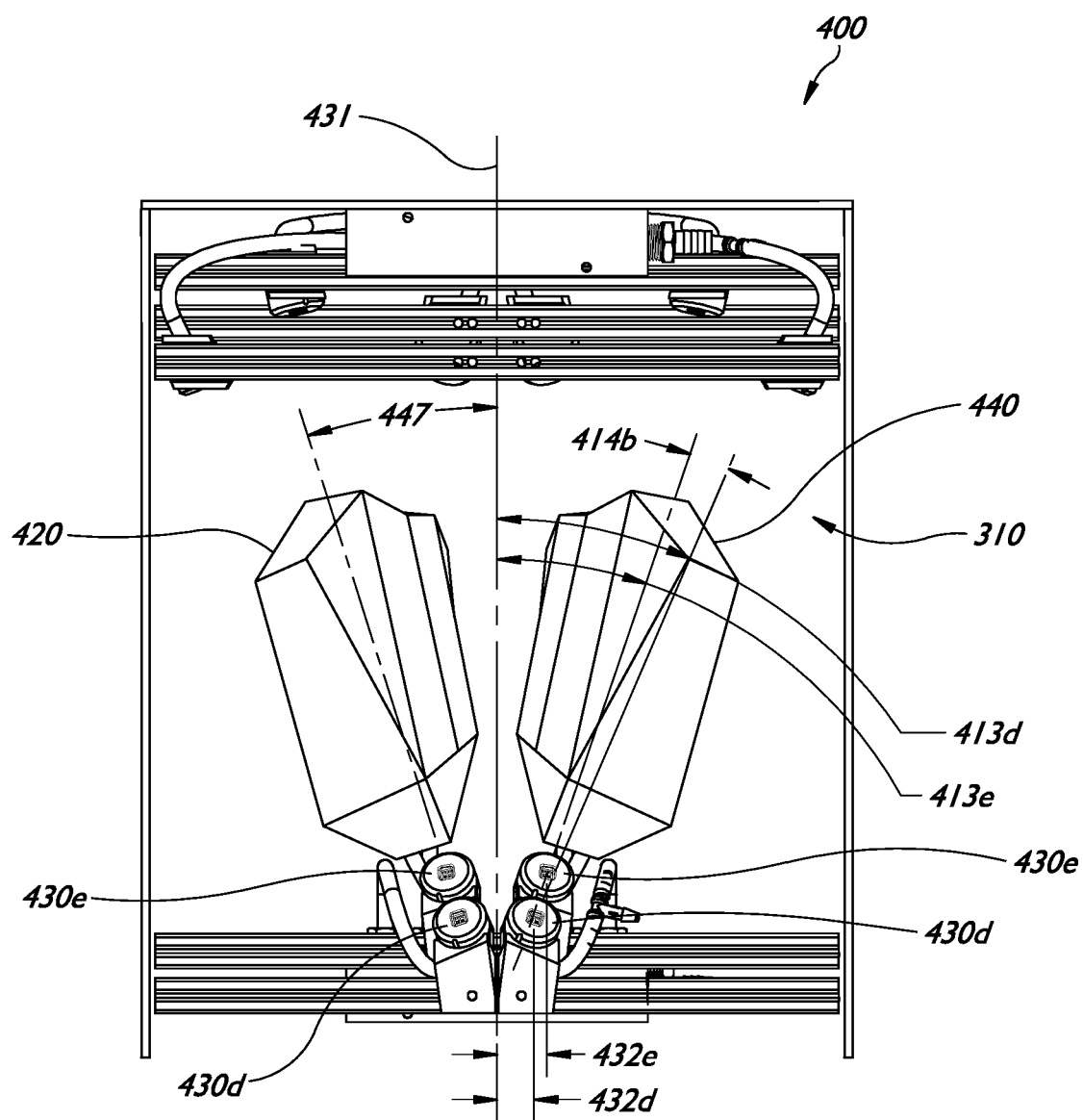
FIGS. 11C and 12C illustrate spray zones and spray devices in a rear view of a spray chamber of the illustrative embodiment of FIGS. 11A and 12A.

In one embodiment as illustrated in FIG. 7C, it has also been discovered to be advantageous to rotate the hands 20 slightly angled apart, e.g., rotating the forearms 44 along the proximal-distal axis 26 (FIG. 7B) to position the thumbs 40 laterally further apart such that the surface plane of the palm 34 and dorsal sides 36 of each hand are about 115 degrees relative to the floor, thus angling the palms of the hands each to an anterior-posterior rotation 25 of about 25 degrees. This provides about 50 degrees of angular separation between the palms 34, thereby reducing the opposing hand's obstruction of spray line of sight from the spray devices 410 and 430 to each palm, thus improving the facing palms' direct line of spray exposure to the spray devices.

It has also been discovered to be advantageous to spread the fingers 38 and thumb 40 apart from each other for static hand sanitizing, thereby further reducing obstructions to direct line of spray exposure from the spray devices 410 and 430 to all areas of the fingers and thumb.

It has also been discovered to be advantageous to achieving the above disclosed goals to provide spray devices 410 and 430 oriented relative to and directed to specific regions of each hand 20. TABLE 1, listed below, and the discussion that immediately follows is directed to describing an illustrative arrangement of the spray devices 40 and the hands 20, particularly the coverage of the hands 20 by each spray device 410 and 430.

TABLE 1

| Spray Device Hand Coverage/Relative Origin | | | | | | | |
|---|---|---|---|---|---|---|---|
| Spray Device 410/430 | Lateral (toward thumb) | Medial (toward little finger) | Anterior (palm side) | Posterior (dorsal/ back side) | Proximal/ Wrist (carpus region) | Central (metacarpal region) | Distal/ Fingers (phalangeal region) |
| a | X | | X | | X | X | |
| b | X | | X | X | | X | X |
| c | X | | | X | | | X |
| d | | X | X | X | X | X | |
| e | | X | X | X | | X | X |

Referring to FIGS. 7A and 7B, an illustrative spray system 400 is shown providing sanitizing of a user's hands 20 with ozonated water 52, illustrated as spray patterns 421. Advantageously, elements of the control system 500 can guide the position and/or orientation of the hands 20 into a bounded area defined within the spray chamber 310, referred herein as a spray zones 420 and 430. In the illustrative embodiment, the position, orientation, and overlapping spray patterns 421 define the spray zones 420 and 430 as bounded areas within which the hands 20 are position to maximize the irrigation coverage of the hands with direct spray of ozonated water 52. The distance from the spray devices 410 and 430 to the spray zones 420 and 430, and thus to the hands 20, is also selected to provide full coverage while minimizing losses in ozone concentration, thus providing simultaneous irrigation coverage of the hands, thereby eliminating the necessity of moving or scrubbing the hands and minimizing the time of irrigation required for sanitizing the hands.

Referring to FIG. 7B, the user's hand 20 includes a proximal wrist 30, also know as a corpus region, a central region 32, also known as a metacarpal region, and distal fingers 38, also known as a phalangeal region. For select embodiments, a portion of the forearms 44 may be included in the scope of the term wrists 30, and therefore hands 20. The user's hands 20 also did defines a lateral thumb side 40 and a medial side 42, i.e., an opposite side adjacent the little finger. Referring to FIG. 7A, the user's hands further define palms 34, i.e., an anterior side, and a dorsal side 36, i.e., a posterior or backside.

As illustrated by both Table 1 and FIGS. 7A and 7B, specific ones of the spray devices 410 and 430 are directed to specific regions of the hands 20. In the illustrative embodiment, spray devices 410 and 430 may each include a fluidic oscillator 411 (not shown) that provides a two-dimensional fluid oscillation centered on a longitudinal axis 412 of the device. In the illustrative embodiment, the fluidic oscillator 411 or other features controlling the spray exiting the spray devices 410 and 430 provide an three-dimensional spray pattern, including an angular spray fan 419a of about 32 degrees about a anterior-posterior 418, and an angular spray fan 419b of about 16 degrees about a proximal-distal axis 435a. Illustrative spray devices 410 and 430 are, for example, available from Bowles Fluidics Corporation of Columbia, Md. Use of such fluidic oscillators positioned and oriented as disclosed effectively achieves the desired combined chemical and mechanical action applied aqueous ozone with the high surface area provided by small uniform particles with a high spin rate, applied by direct irrigation to the entire surface of the hands, efficiently loosening and lessening the microbe load; however, other forms of application of aqueous ozone may be used if similar dispensing of aqueous ozone is achieved.

In the illustrative embodiment, and as shown in FIGS. 7A-B and FIGS. 9A-10B, the spray devices 410a-c and 430a-c are located in a chamber upper half 312, for example, coupled to chamber top 314, and the spray devices 410d-e and 430d-e are located in a chamber lower half 320, for example, coupled to chamber bottom 322. Additionally, the spray devices 410a/430a, 410a/430d, and 410a/430e are located anterior to, e.g., in-between, the hands 20, and the spray devices 410b/430b and 410c/430c are located posteriorly, e.g. outside of, the hands 20. As can be noted for the spray devices 410b and 430b, selected spray devices may also have the longitudinal axis 412a aligned with, or about aligned with, the lateral-medial axis 22 of the hands 20. This alignment depends on the desired relative position and anterior-posterior rotation 25, for example as shown in FIG. 7A with palms facing and parallel and contrasted with FIG. 7C with palms slightly angled apart at the top, that the control system 500 guides the user's hands to.

The combination of the location and rotational position of the spray devices 410 and 430 and the position and rotational orientation of the hands 20 to which they are guided by the control system 500 of the illustrative embodiment is shown in FIGS. 7A and 7B (and alternatively FIGS. 7C and 7B) and FIGS. 11A-12C and is further described below. The spray devices 410a-b/430a-b have a direct spray line of sight with the palms 34, the spray devices 410c/430c has a direct spray line of sight with the dorsal side 36, and the spray devices 410d-e/430d-e have direct spray line of sight to the medial 42 and portions of the palm 34 and dorsal side 36.

As illustrated in the Figs. and described in Table 1, the spray devices 410a/430a are directed to the wrist 30 and may also be directed to one or both of the forearm 44 and the central region 32. The spray devices 410b/430b are directed to the central region 32 and may also be directed to at least a portion of the fingers 38. The spray devices 410c/430c are directed to the fingers 38 and may also be directed to a portion of the central region 32. The spray devices 410e/430e are directed to the fingers 38, and may also be directed to a portion of the central region 32. The spray devices 410d/430d are directed to the wrist 30 and at least a portion of the central region 32, and may also be directed to a portion of the forearm 44.

Because the coverage of the hands 20 with direct spray from the spray devices 410 and 430 is more consistent than is subsequent runoff of ozonated water 52, and because ozone concentration is reduced by mechanical action, the illustrative embodiment maximizes the direct spray coverage of the hands 20.

To further facilitate full coverage with the ozonated water 52, elements of the control system 500, including the user interface 584 and optionally the hand sensors 590, may also guide the user to separate the fingers 38 and thumb 40, for example, as is illustrated in FIG. 7B, or to a higher degree of separation than is illustrated.

The following description along with FIGS. 11A-12C disclose specific features of the illustrative embodiment of the spray system 400 to achieve the above discussed aspects of spray coverage. A device anterior-posterior datum plane 431 is located centrally in the spray system 400 and the sanitizing chamber 310. A device proximal-distal location datum plane 433a is located at a proximal (front) edge of the spray system 400. A device lateral-medial datum plane 435a is located at a proximal, bottom (medial) edge of the spray system 400 and the spray chamber 310, for example, about 34 inches above the floor level.

A spray zone proximal-distal datum plane 433b is located at a proximal (front) edge of the spray chamber 310. A spray zone lateral-medial datum plane 435b is located centrally in the spray chamber 310, for example, aligned with a center of the openings 372a-b and sloped downward, for example, about 4 inches above the bottom edge of the spray system 400 and the spray chamber 310, and sloped downward about 15 degrees into spray chamber.

The spray devices 410a-c/430a-c are located in the chamber upper half 312 and have an angular displacement 414a about a proximal-distal axis 417 that spans within a range of 30 to 50 degrees, for example, about 45 degrees, and an angular displacement 416a about a anterior-posterior axis 418 that spans within a range of 30 to 50 degrees, for example, about 40 degrees. The spray devices 410d-e/430d-e are located in the chamber lower half 320 and have an angular displacement 414b about the proximal-distal axis 417 that spans within a range of 0 to 10 degrees, for example, about 3 degrees, and an angular displacement 416b about the anterior-posterior axis 418 that spans within the range of 0 to 10 degrees, for example, about 4 degrees.

Figure 12A:
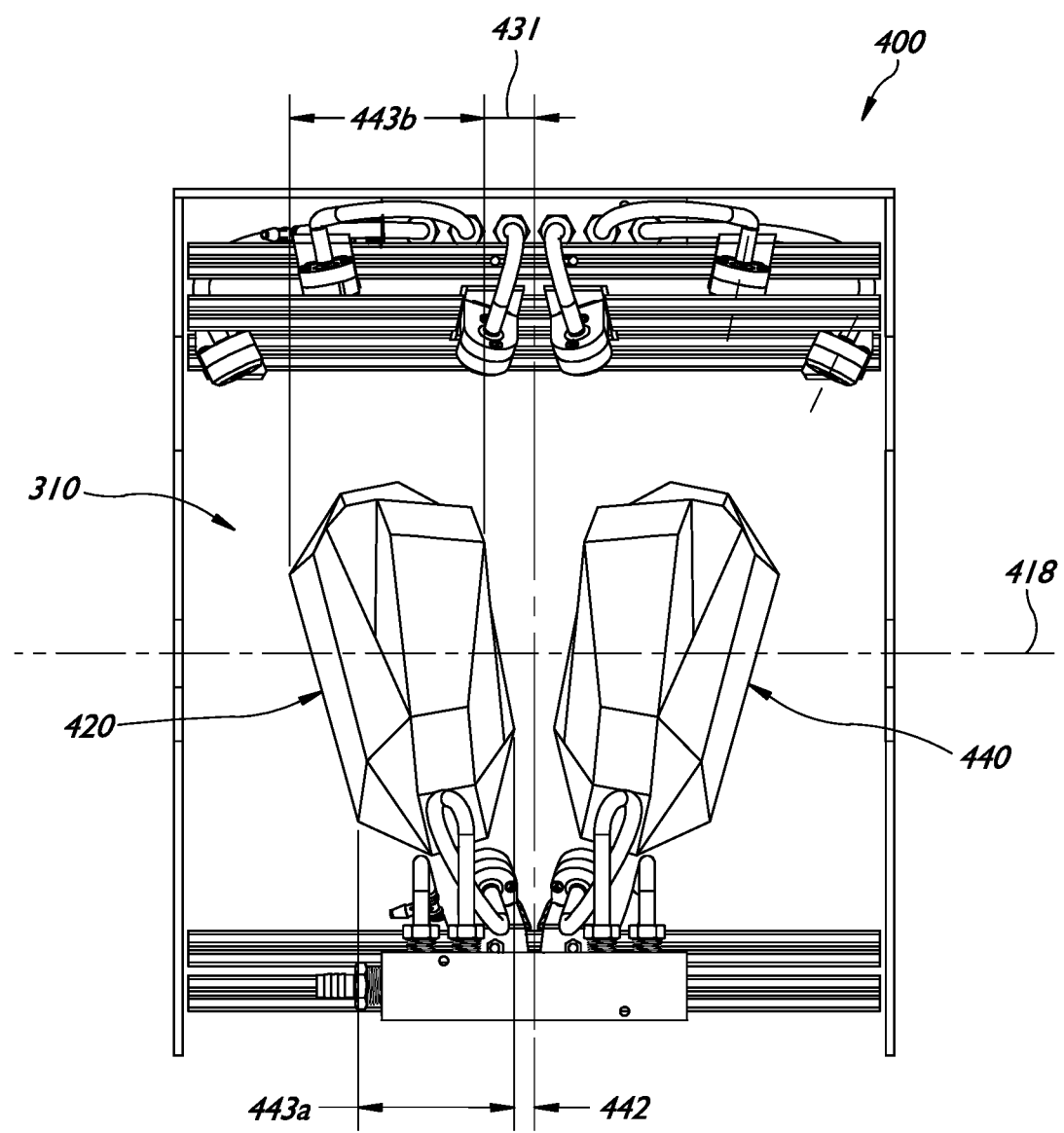
Figure 12B:
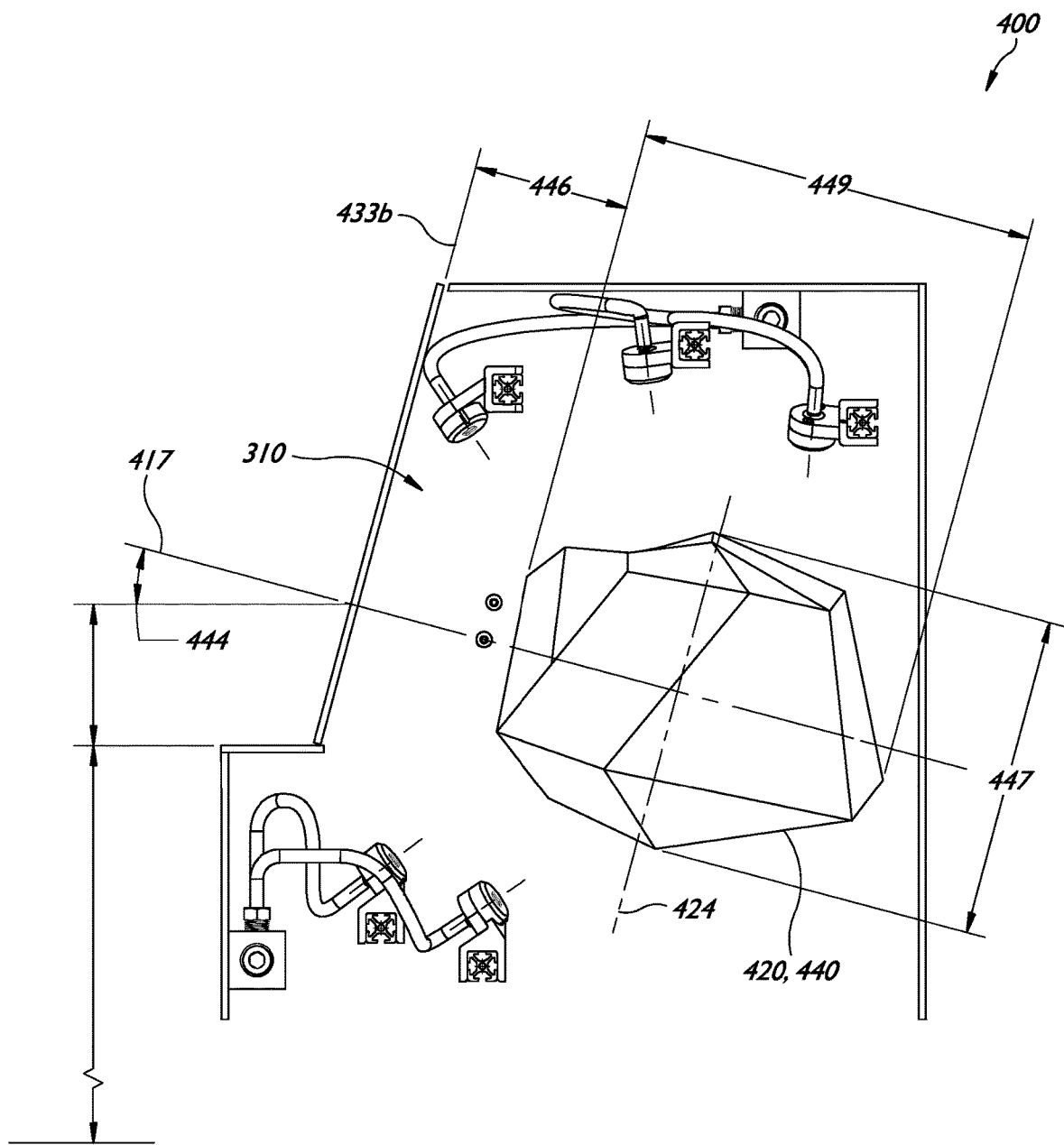
Figure 12C:
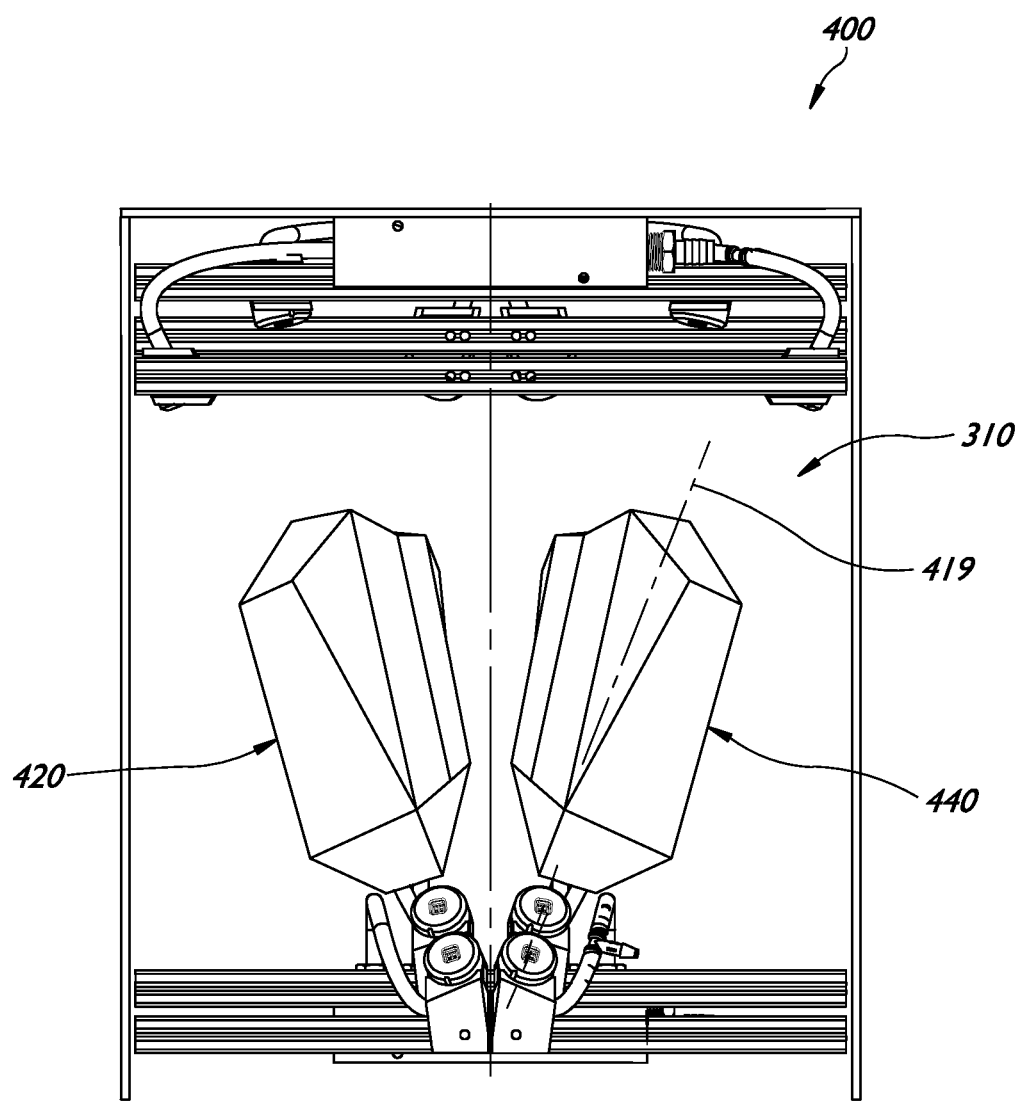

Referring now to FIGS. 12A-12C, a left spray zone 420 defined within the sanitizing chamber 310 specifies the area within which the left hand 20a is positioned and oriented by the control system 500, and a right spray zone 440 specifies the area within which the right hand 20b is positioned and oriented by the control system. In the illustrative embodiment, each of the left and right spray zones 420 and 440 encompass less than about 320 cubic inches.

Each of the left and right spray zones 420 and 440 define a proximal-distal axis 417 having a zone anterior-posterior slope 444 of about 15 degrees about the anterior-posterior axis 418, sloping downwardly in a direction extending from the pair of openings 372a-b and into the sanitizing chamber 310.

Each of the left and right spray zones 420 and 440 define a lateral-medial axis 424 that is oriented a zone lateral-medial slope 447 of between about 10 degrees and about 25 degrees about the anterior-posterior axis 418 and is sloped outwardly in a direction extending from the bottom toward the top of the pair of openings 372a-b.

Each of the left and right spray zones 420 and 440 define an anterior zone edge 442 of about 0.5 inches from the center of the openings 372a-b, a proximal zone edge 446 of about 4 inches from the openings, a lateral-medial zone center 441 of about 4 inches above the bottom edge of the spray system 400 and the spray chamber 310.

Each of the left and right spray zones 420 and 440 can define along an anterior-posterior axis 418 a lateral zone anterior-posterior span 443a of about 3.5 inches and a medial zone anterior-posterior span 443b of about 4.5 inches, define along an lateral-medial axis 424 a zone lateral-medial span 447 of about 8 inches, and define along a proximal-distal axis 417 a zone proximal-distal span 449 of about 10 inches.

In the illustrative embodiment of spray system 400, the spray device 430a has an anterior-posterior location 432a of about 1.1 inches, a proximal-distal location 434a of about 6.2 inches, and a lateral-medial location 436a of about 8.3 inches. The spray device 430b has an anterior-posterior location 432b of about 4.5 inches, a proximal-distal location 434b of about 11.0 inches, and a lateral-medial location 436b of about 9.7 inches. The spray device 430c has an anterior-posterior location 432c of about 6.6 inches, a proximal-distal location 434c of about 15.2 inches, and a lateral-medial location 436c of about 8.0 inches. The spray device 430d has an anterior-posterior location 432d of about 0.8 inches, a proximal-distal location 434d of about 4.2 inches, and a lateral-medial location 436d of about −3.1 inches. The spray device 430e has an anterior-posterior location 432e of about 1.1 inches, a proximal-distal location 434e of about 6.9 inches, and a lateral-medial location 436e of about −4.1 inches. The spray devices 410a-e have corresponding mirror image locations to those of spray devices 430a-e.

The spray device 430a has a rotational location 413a of about −18 degrees about the proximal-distal axis 417 and relative to the anterior-posterior datum plane 431, and a rotational location 415a of about 41 degrees about the anterior-posterior axis 418 and relative to the proximal-distal datum plane 435b. The spray device 430b has a rotational location 413b of about 11 degrees about the proximal-distal axis 417 and relative to the anterior-posterior datum plane 431, and a rotational location 415b of about 68 degrees about the anterior-posterior axis 418 and relative to the proximal-distal datum plane 435b. The spray device 430c has a rotational location 413 of about 26 degrees about the proximal-distal axis 417 and relative to the anterior-posterior datum plane 431, and a rotational location 415 of about 80 degrees about the anterior-posterior axis 418 and relative to the proximal-distal datum plane 435b. The spray device 430d has a rotational location 413 of about 23 degrees about the proximal-distal axis 417 and relative to the anterior-posterior datum plane 431, and a rotational location 415 of about −52 degrees about the anterior-posterior axis 418 and relative to the proximal-distal datum plane 435b. The spray device 430 has a rotational location 413 of about 19 degrees about the proximal-distal axis 417 and relative to the anterior-posterior datum plane 431, and a rotational location 415 of about 49 degrees about the anterior-posterior axis 418 and relative to the proximal-distal datum plane 435b.

The span between the upper devices 410a-c/430a-c and the lower devices 410d-e/430d-e ranges between about 11 and 14 inches, thereby limiting the transient of the ozonated water 52 from the spray devices to the hands 20 to between less than 5.5 inches and less than 7 inches. This geometry for the spray devices 401a-e/430a-e has been discovered to enable a wide range of hand sizes and minimizing the distance between upper and lower spray devices increases efficiency by minimizing the loss for the ozonated water of dissolved ozone to gaseous ozone and reduces the exposure to gaseous ozone.

Sanitizing System Control

Figure 17:
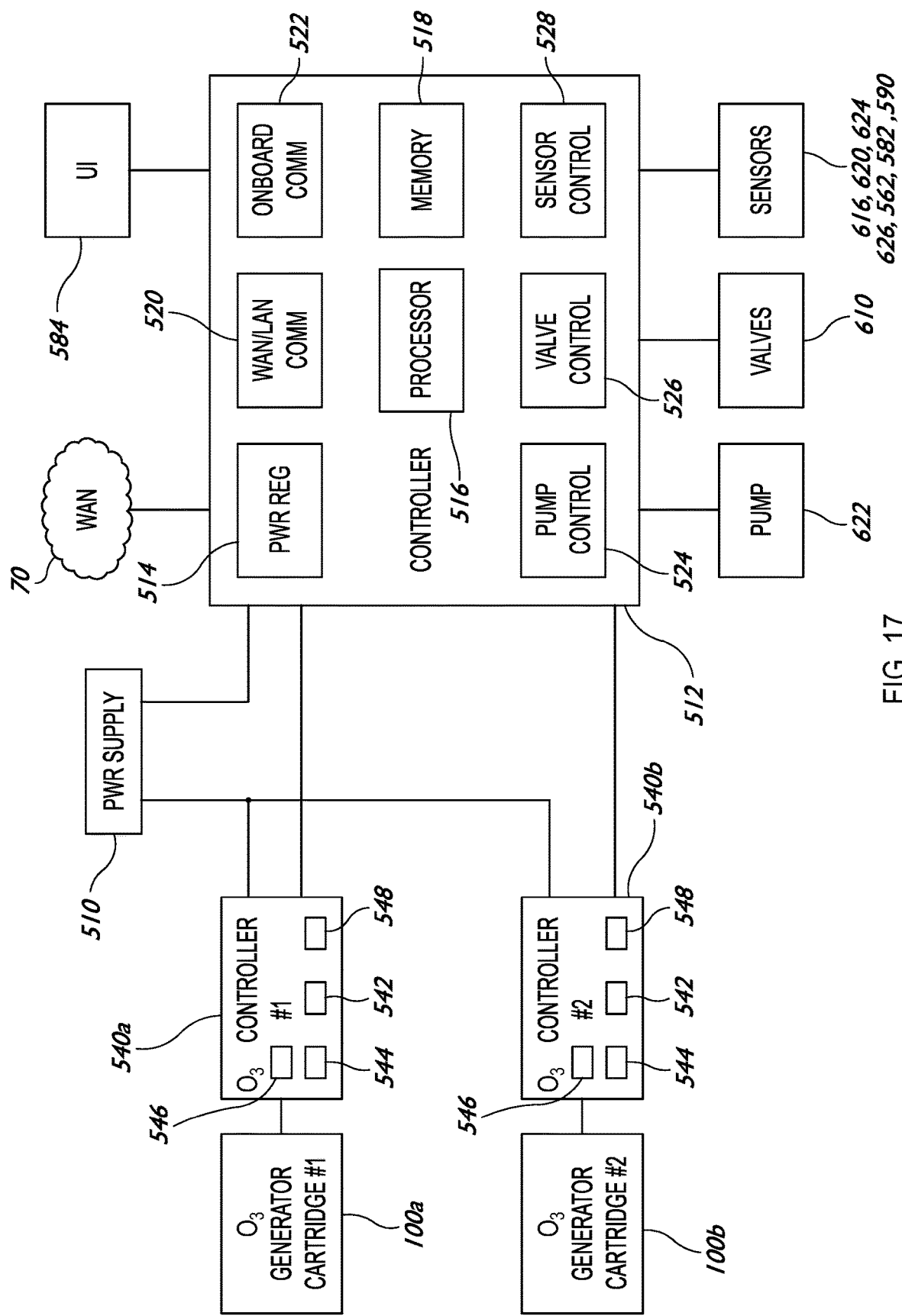
FIG. 17 illustrates an electrical schematic block diagram of an illustrative embodiment of an aqueous ozone sanitizing system according to the present disclosure.

Referring to FIGS. 4 and 17, the control system 500 includes a power supply 510, a controller 512, ozone controllers 540, and a user interface 584. The control system 500 controls all aspects of the operation of and user interaction with aspects of the hand sanitizer 300, particularly the aqueous ozone generators 100a-b and the spray system 400, including the delivery of untreated water supply 500 to the ozone generators by the pump 622, valves 610, and sensors 616, 620, 624, and 626, and including the delivery of and desired ozone concentration level of the ozonated water 52 to the spray chamber 310. The controller 512 may also provide user guidance and or sensing, for example, in a sanitizing process 700 illustrated in FIG. 18 and described below, controller 512 verifies that a user's hands 20 are positioned within the spray zones 420 and 440 for the duration of a sanitizing cycle. Components of the control system 500 may reside within the hand sanitizer 300, the aqueous ozone generators 100a-b, or distributed between the hand sanitizer 300 and the aqueous ozone generators 100a-b.

The control system 500 may optionally implement identity, data logging, fault detection, and other local and/or cloud-based supervisory and operational control functions to ensure proper operation of the hand sanitizer 300, including the ozone generators 100 and user compliance with the hand sanitizing 300 operating requirements and/or external compliance requirements.

The controller 512 in the illustrative embodiment may be a digital control system using a processor 516 and memory 518 and may also include analog circuits, for example power regulator 514 and various actuator and sensor controls. The controller 512 can be powered by the power supply 510, for example a medical grade 500 W AC to DC power supply. The controller 512 may also include a power regulator 514 to further condition and regulate power received from the power supply 510 as required for components of the control system 500 and the water supply system 600, including the controller 512 and the ozone generator controllers 540.

For controlling the untreated water supply 50, the controller 512 can includes a pump control circuit 524 for controlling the operation of the pump 622, and may provide variable control, for example of flow rate and/or pressure of the untreated water supply 50. If the water supply system 600 includes controllable valves such as supply valve 610 and drain valve 618, the controller 512 also can include a valve control circuit 526 for controlling the operation of the valves. For example, in the illustrative embodiment of the spray system 400, each spray device 410a-e and 430a-e requires aqueous ozone delivered at at least 4 psi for proper operation, which can be monitored by measure water pressure or flow rate for a given embodiment of the system 300.

The water supply system 600 may also include various sensors, for example, a water level sensor 616 to measure the volume of untreated water held within the holding tank 614, a water temperature sensor 620, a flow meter 624, and a pressure sensor 626. If the water supply system 600 includes any of these optional sensors, the controller 512 may include a sensor control circuit 528, for example, that provides conditioned signals for the sensors and receives data signals indicative of measurements made by the sensors.

The pump control 524, valve control 526, and sensor control 528 may be in data communication with the processor 516, for example, using an onboard communication circuit 522. In one embodiment, the processor 516 may include aspects of the control circuits 524, 526, and 528, for example, as is common in microcontrollers.

The ozone generator controllers 540a-b may be integral with the controller 512, comprise one or more daughter boards, or comprise a separate board located with the hand sanitizer 300 or the housing 102 of the aqueous ozone generator 100. The illustrative embodiment the hand sanitizer 300 includes an ozone generator controller 540a for the right aqueous ozone generator 100a and an ozone generator controller 540b for the left aqueous ozone generator 100b. Each ozone generator controller 540a-b may include, for example, a driver 542 for powering the ozone generating cells 210a-d, for example a constant current driver such as a buck-boost constant current switching regulator, a power monitor 544, a polarity swap circuit 546, and a sensor circuit 548.

In the illustrative embodiment the ozone generator cells 210 of the aqueous ozone generators 100 are electrolytic, and the polarity swap circuits 546 enable periodic changing of the polarity delivered to the electrodes of the cells, for example swapping polarity between each hand sanitation cycle. The level of ozone generated by the ozone generator cells 210 is a function of power supplied, therefore the power monitor 544 facilitates additional ozone concentration control. Additionally, degradation of the ozone generating cells 210 because of usage or fault may be determined in part by an increase in voltage for given current level, thereby the power monitor 544 being used for detecting degradation or failure of one or more ozone generating cells 210 when an increased voltage is detected beyond a reasonable range for a given current level. In the illustrative embodiment, the ozone generator cells 210 can be driven by a range of at least 0-1.2 amps each, and with four ozone generator cells 210 each driven by a constant current of 410 milliamps, each aqueous ozone generator 100 produces a concentration of 0.8 ppm of aqueous ozone, with an observed typical voltage of 9-12 volts indicating normal ozone generator cell 210 operation. An elevated observed voltage, for example, 20-25 volts, or above 22 volts indicated degraded generator cell 210 operation. In detecting a degrading or degraded cell 210 in this way, operation of ozone generator 100 and system 300 may optionally continue by removing a degrading or degraded cell form operation and using only the non-faulted cells. Additionally, and optionally, controller 512 may store and/or communicate an alert message, for example, to a remote server 80, that an impending change of ozone generator 100 will be required.

The sensor circuits 548 each provide power to and receive data signals from one of the inlet sensor 230 and outlet sensors 240a-b of the aqueous ozone generators 100. For example, an oxidation-reduction potential sensor or other type sensor is used for inlet and outlet sensors 230 and 240a-b to measure ozone concentration, providing controller 512 with closed loop control of the production provided by aqueous ozone generators 100. For example, the data signal from at least one ozone inlet sensor 230 can be compared by the ozone controller 540 or the controller 512 to the data signal from at least one outlet sensor 240a-b to determine the ozone concentration provided by the aqueous ozone generators 100.

In one embodiment, a second inlet outlet sensor 240b is provided to validate the data signals received in determining the ozone concentration. Additionally, measurement of the ozone concentration in the ozonated water 52 may allow the controller 512 to detect a degradation or failure of one or more aqueous ozone generating cells 210a-d in the event the supplied power provided by the aqueous ozone controllers 540a-b does not provide a measured ozone concentration as expected. For example, a testing state of the hand sanitizer 300 may provide individual powering of each ozone generating cell 200a-d for each aqueous ozone generator 100a-b in order to detect a degraded or failed cell, and may enable continued use of the aqueous ozone generator 100a-b, for example, by powering and relying on the remaining fully functioning cells to provide the desired level of ozone concentration.

The generator controllers 540a-b may include an individual driver 542, power monitor 544, and polarity swap circuit 546 for each of the ozone generator cells 210a-d. For example, in the illustrative embodiment, the aqueous ozone generator 100 includes up to four ozone generating cells 210a-d, therefore for separately controllable drivers 542, power monitors 544, and validity swap circuits 546 are included with each ozone controller 540. Other embodiments may include additional or fewer ozone generating cells 210a-d per generator 100.

In the illustrative embodiment of ozone generator 100a-b, as will be discussed further below, the ozone generator cells 210a-d are each exposed to a separate waterflow pathway and the separate pathways are fluidly arranged in parallel. It is thought that the duty life of the ozone generating cells 210a-d, and thus the generator 100a-b, can be lengthen in this parallel arrangement as each may be simultaneously operated by the ozone controller 540a-b at a lower power level to achieve a desired ozone concentration than if fewer cells were used, or if the cells were arranged serially. Additionally, if the desired ozone concentration can be achieved by powering a subset of the ozone generating cells, the duty life may also be lengthened by the ozone controller 540 alternating selectively powering only a subset of the cells. The later may also be used to keep a generator 100 in service that has suffer a degradation or failure of one of the ozone generating cells 210a-d as the load can be picked up by the remaining fully functional cells without changes to the hardware or water passageway 290.

In the illustrative embodiment of the hand sanitizer 300, a user interface 584 is operated by the controller 512 in coordination with the presence sensor 582 and the hand sensors 592 to coordinate the control of the hand sanitizer 300 with the user, particularly the position and orientation of the user's hands 20 within the spray chamber 310. The presence sensor 582 may be, for example, a capacitive, time-of-flight, or other distance, occupancy, or proximity detection sensor. The presence sensor 582 can be used to detect that a user has approached the hand sanitizer 300 for use. For example, in one embodiment, the controller 512 and presence sensor 582 can be used to wake the hand sanitizer from a standby or low-power state and transition to a ready state, including providing guidance and/or status information to a user via the user interface 584 and/or other indicating device.

In the illustrative embodiment, the controller 512 will not transition from the ready state to irrigation state unless both a hand sensor 592 detects a user's hand in position with the spray chamber 310 and the presence sensor 582 detects a person within sufficient proximity of the spray chamber 310 to use the sanitizer, for example within 18 inches, within 12 inches, or between 6 and 12 inches. Requiring detection by both a hand sensor 592 and the presence sensor 582 eliminates false detections to due water splash residue that could occur if initiation of the irrigation state required only detection by the hand sensor 592.

Figure 18:
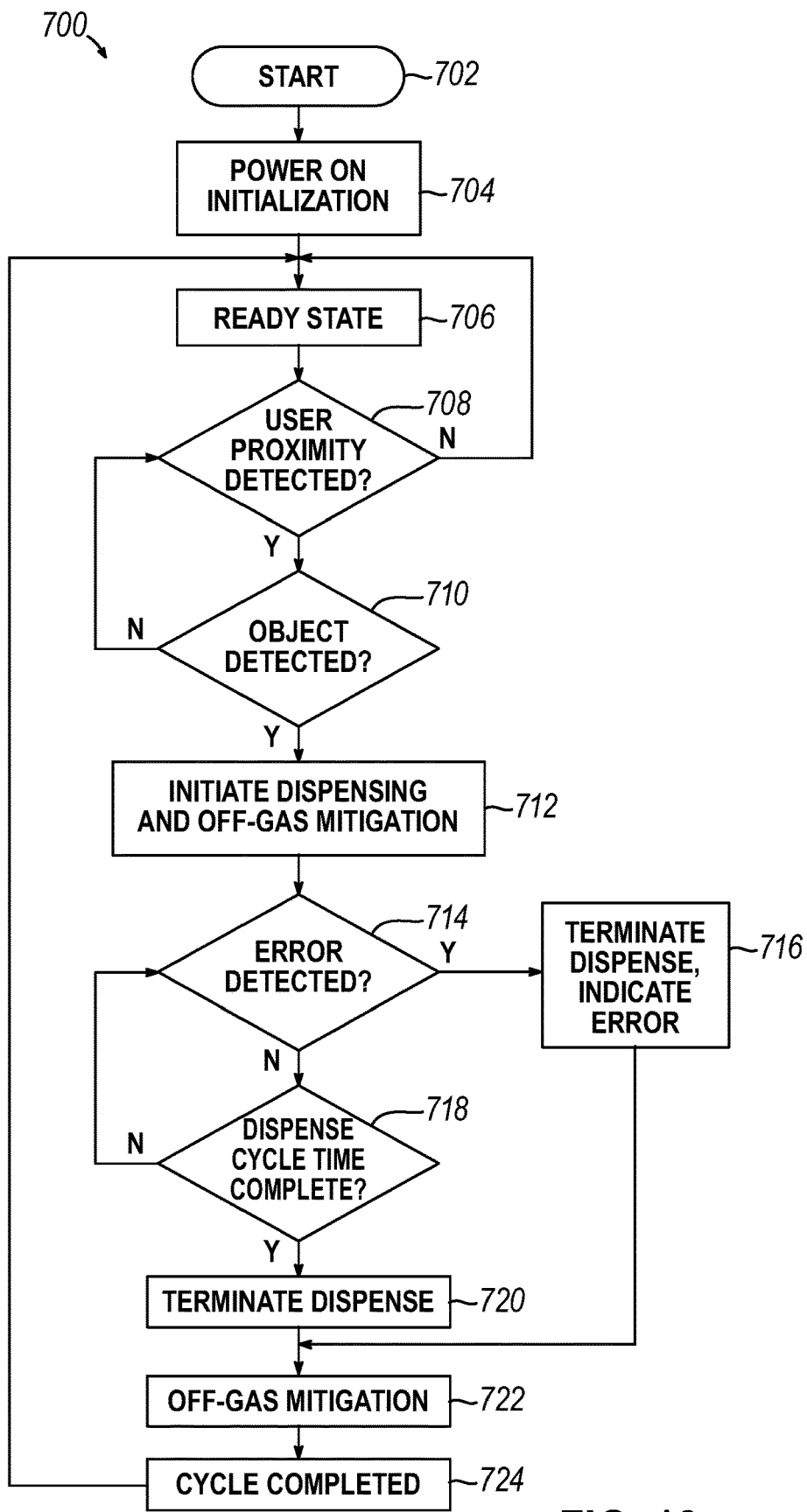
FIG. 18 shows an illustrative process for the operation of the illustrative embodiments of FIGS. 1A-B, 4, and 17.

For example, as illustrated in FIG. 2, the user interface 584 indicates states of the hand sanitizing process. The user interface 584 can be a fixed graphic display that is not lighted or animated, may be lighting 586, for example with varying colors and steady and flashing states, may be a dynamic graphic display, for example, including fixed icons with selective backlighting, color, brightness, steady, or flashing illumination of the fixed icons, and/or a display that is not fixed, for example an LCD or other display unit. For example, as illustrated in FIG. 18, operating steps or states of a hand sanitizing process, are indicated. For example, a first state icon instructs insertion of a user's hands 20 upon detection of the presence of the user by presence sensor 582. The hand sensors 590, for example located at an interior chamber top 314 of the sanitizing chamber 310, may be used to detect the movement into and/or position and orientation within the spray zones 420 and 440 discussed above in describing the spray system 400.

Illustrative hand sensors 590 are capacitive, electro-optical, time-of-flight and other sensors known in the art that are capable of detecting presence, location, and/or motion, and that may provide image data from which detection can be determined. For example, in the illustrative embodiment, a hand sensor 590 is located above each of the proper positions for the left and the right hands, for example, above left spray zone 420 and above right spray zone 440, and calibrated to detect when the left and right hands are located within a proper position laterally and vertically, for example, within the left and the right spray zones. The illustrative hand sensor is a time-of-flight sensor, for example a laser-ranging sensor module such as VL53LOX available from STMicroelectronics of Edina, Minn. The identity sensor 580 may include one or more RF antennas capable of detecting an identification or access card at sufficient range so that a user need not specifically swipe an RFID or other identity card while using system 300.

In an alternative embodiment, the hand sensors 590 include a linear infrared array capable of detecting motion and providing a primitive image that can be processed to determine motion, position, orientation, and even finger and thumb spread. For example, the hand sensors 590 may be sensors such as those used for hand gesture detection, for example, sensors available from Neonode Technologies AB, of Stockholm, Sweden.

Upon the controller 512 and hand sensors 590 determining correct position and/or orientation of the hands 20, a second icon state of user interface 584 may be displayed, indicating activation of the spray system 400. For example, irrigation of the hands 20 with ozonated water 52 for a preset duration of time, water volume, or total ozone exposure. Advantageously, if the hand sensors 590 detect improper position or orientation of the hands 20 during the sanitizing state, the user interface 584 can provide an indication to the user to take corrective action. The indication may be a change in the state icon, display of a different icon, or an audible or other indication. Upon successful completion of the sanitizing state, the user interface 584 can display a third completion state, indicating the user that the hand sanitizing cycle has been successfully completed and hands 20 can be removed from the sanitizing chamber 310.

In one embodiment, a visible light indication separate from the user interface 584 may be used with one or more states to indicate a status or instruction to the user. For example, one or more lights turned on, off, flashed, or changed in color or brightness, for example within the sanitizing chamber 310, may indicate a ready state awaiting the insertion of the hands 20, a state indicating the hands 20 are in the proper position and orientation, or completion of the hand sanitizing state.

The indication of a successful completion of a hand sanitizing cycle may also include consideration of other aspects of the hand sanitizer 300 in addition to the position orientation of the hands, for example measurement by the control system 500 of the desired ozone concentration, flow rate, and/or duration.

In on embodiment, the control system 500 includes an gaseous ozone sensor 562 to detect a level of gaseous ozone concentration exhausted through the fan screen 346, for example, to ensure proper functioning of an ozone filter 348 and fan 560 and capturing or neutralizing gaseous ozone drawn from the spray chamber 310. For example, detection of an excessive gaseous ozone level by the controller 512 and gaseous ozone sensor 562 could lockout operation of the spray system 400, including aqueous ozone generators 100a-b until a control system 500 flag indicating maintenance is required is reset by authorized personnel.

In at least one embodiment, the control system 500 provides a security feature which prevents operation of the spray system 400 if one of the aqueous ozone generators 100a-b is not detected, is not properly authenticated, or has not been paired for use with the hand sanitizing system 300. For example, the aqueous ozone generators 100a-b may include a memory device 254 and/or a digital security device 256 that the controller 512 can communication with. A startup or other check of the hand sanitizing system 300 can include an onboard or offboard, for example, via WAN 70 and remote server 80, security check to verify that the aqueous ozone generators 100a-b are authentic, properly paired for use with the hand sanitizing system 300, and can therefore be relied upon to provide a desired level of ozone concentration or to detect an improper level of ozone concentration. Such a security feature can use part serial numbers, encryption, block-chain technology, or other technology known in the art and incorporated into one or both of the aqueous ozone generators 100a-b and the control system 500 to ensure operation of the hand sanitizing system 300 is prevented if critical components are not found and validated.

Referring to FIG. 19, a display plan view of various additional or alternative display icon designs for user interface 584 is shown. For example, a number of alternative status indicators for various states and conditions of the hand sanitizer 300 and user's hands 20 are illustrated, including indications of the position and orientation of hands 20, sanitizing cycle time elapsed or remaining, successful and unsuccessful cycle completion, and a user identity (not shown).

Referring to FIG. 4, the control system 500 may also include a personnel identity sensor 580, including, for example, a sensor capable of reading an optical barcode, RF, NFC, or other identification badge or access card, or an imaging device capable of using facial recognition or other biometric identity indicators. The identity sensor 580 may include one or more RF antennas capable of detecting an identification or access card at sufficient range so that the user's ID on their body can be captured passively upon use of the sanitizer 300 without the user having to actively swipe the ID near the identity sensor.

The advantage of incorporating user identity into the control system 500 is to limit access to and/or track the use and compliance regarding the use of the hand sanitizer 300. For example, the processor 512 may be capable of storing in memory 518 or transmitting via the WAN/LAN communication circuit 520 various data logging information that relates to any of system performance, system use, and successful or unsuccessful completion of the sanitizing cycle, including user identity, times, frequency, and outcome of the uses.

Advantageously, in at least one embodiment, a local area network or wide area network 70 may be used to communicate data logging and other data associated with the controller 512 with a personal computing device 82, for example a handheld smart device, or a server or other remotely located computing device 80.

Note that FIG. 17 includes elements of the control system 500 and water delivery system 600 that are optional and may not be included in various embodiments of an aqueous ozone sanitizing system according to the present disclosure. Optional elements include but are not limited to: WAN/LAN transceiver 520, valve controller 526, sensor controller 528, gaseous ozone sensor 562, ID reader 580, presence sensor 582, user interface 584, lighting 586, UV light 588, hand sensors 590, supply valve 510, inlet filter 612, holding tank 614, water level sensor 616, drain valve 618, temperature sensor 620, flow meter 624, pressure sensor 626, and releasable coupling 628.

Of note, the temperature of water for most water supplies does not appear to have significant bearing on either the amount of ozone produced, or the amount of decay in the brief distances and time between generation and application in the illustrative embodiments, so it is contemplated that water temperature measurement or control is not required for many of the applications and uses discussed herein.

Referring to FIG. 18, a hand sanitizing process 700 is illustrated that may be executed by the control system 500, for example the controller 512, for example, including the processor 516. The process begins at step 702. At step 704, the controller 512 may enter a startup state, for example, upon powering on of the system 500, or alternatively in another embodiment, upon the presence sensor 582 and/or identity sensor 580 detecting close proximity of a user. At step 704, the processor 512 may power additional portions of the control system 500, for example, the user interface 584, the pump 622 for priming, and possible direct diagnostic or other system checks of the electrical system 500 and water supply system 600.

Upon the controller 512 determining that the startup state is complete, a step 706 provides a ready state. The ready state of controller 512 may include, for example, an indication on the user interface 584 to the user to insert the hands 20 into the sanitizing chamber 310, for example, indicator lighting 586 illuminating the sanitizing chamber 310 with a steady white light.

In step 708, controller 512 determines using presence sensor 582 whether a user is in close proximity of the front cover 370, for example, in proximity to insert hands into the chamber 310, for example, within 18 inches, within 12 inches, or between 6-12 inches. If not, the process 700 continues at step 706. The controller 512 may also capture user identity information using identity reader 580 for later reporting of system 300 use by the user, for example, at steps 716-724.

At step 710, upon the controller 512 detecting movement within the sanitizing chamber 310, for example, positioning of a hand with the left and/or right spray zones 420 and 440 detected by the hand sensors 590, the process will continue to step 712, else return to step 708. In a step 710, which provides a hand insertion state, user interface 584 feedback or other guidance to the user may be provided regarding hand position and orientation, including based on detection by the hand sensors 590 whether hand position and/or orientation is correct or incorrect. Upon the controller 512 determining correct hand position and orientation, or after expiration of a delay timer, the process 700 continues to step 710.

At step 710, a dispensing/sanitizing state is provided by the controller 512. For example, ozone off-gas mitigation is initiated, including for example powering fan 560, the pump 622 is activated to provide untreated water supply 52 to the aqueous ozone generators 100, and the ozone generator controllers 540 are provided power and control sensing for the ozone generator cells 210a-d. The ozone generators 100 thereby provide ozonated water 52 to the spray system 400, and spray devices 410 and 430 irrigate the hands 20. The sanitizing state at step 712 may provide an indication of elapsed time, remaining time, and/or an indication of hand position and orientation. Additionally, indicator lighting 586 can illuminate the chamber 310 with a steady teal or aqua light during dispensing. At Step 714, optionally an elapsed time may be paused and optionally ozonated water 52 flow may be stopped in the event the controller 512 and hand sensors 590 detect movement and/or improper position and orientation of the hands 20 relative to the spray zones 420 and 440. Additionally, or alternatively, after detection of correction or after a preset delay, the duration count timer may continue, including completion of the sanitizing state at step 718 once the selected duration of time is completed, for example, 7 seconds. Or alternatively, upon detection of movement and/or improper position, or a fault of the system 300, the controller 512 may proceed to step 716 providing an alert state to the user and/or the remote server 80 that the sanitizing process 700 is incomplete, including for example, indicator lighting 586 illuminating the chamber 310 with a flashing amber light.

Upon successful completion of the sanitizing state for the selected duration of time, at step 720 a dispense/sanitization completion state of the controller 512 removes power from the aqueous ozone generators 100 and the pump 522. Step 720 may optionally provide an indication that the sanitizing state is complete and/or that hands 20 may be removed from the sanitizing chamber 310, for example, the user interface 584 may indicate successful completion, for example, indicator lighting 586 turning off the illumination within the chamber 310, indicating to the user their hands may be shaken to remove water and withdrawn from the openings 372a and 372b, and the controller 512 may optionally provide a 3 second delay before changing the indicator lighting 586 to a ready state in accordance with step 706. At step 720, ozone off-gas mitigation continues for a present period of time, for example, 18 seconds, and/or until controller 512 receives a signal from gaseous ozone sensor 562 that mitigation is complete. Optionally, process 706 can continue to step 724 while the controller 512 monitors ozone off-gas mitigation complete as a new cycle could be started at step 706 before completion of mitigation.

The sanitizing control process 700 may also include other steps, for example step 724 may provide a message mode state of the controller 512 that indicates information relating to a maintenance, troubleshooting, fault, or other state or data indicating that execution of step 702 through 710 is inhibited, including via user interface 584, and/or via WAN/LAN transceiver 520, including to remote server 80 or personal computer device 82. After completion of step 724, the process 700 continues at step 706.

Each of the steps 702-724 illustrated in FIG. 18 also list other additional or alternative substrates and/or indications provided by the user interface 584 or other portion of the control system 500.

Aqueous Ozone Generator Cartridges

Figure 14A:
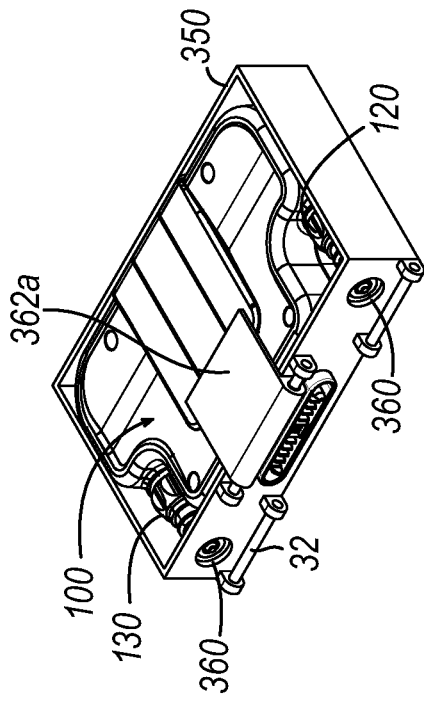
FIG. 14A illustrates a docking receptacle portion of an illustrative embodiment of an aqueous ozone sanitizing device with a locking mechanism for the aqueous ozone generator according to the present disclosure.
Figure 14B:
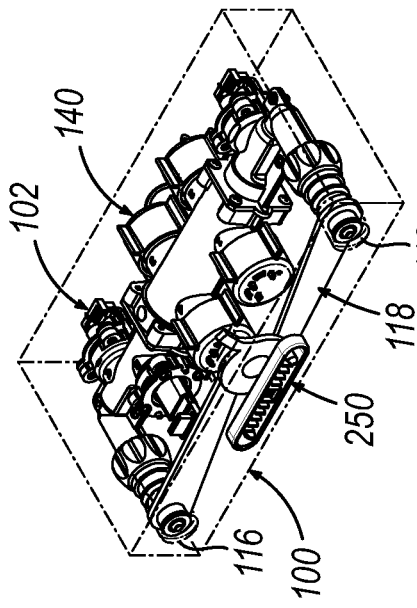
FIG. 14B illustrates an illustrative embodiment of the aqueous ozone generator with a locking mechanism for engaging the docking receptacle according to the present disclosure.
Figure 13:
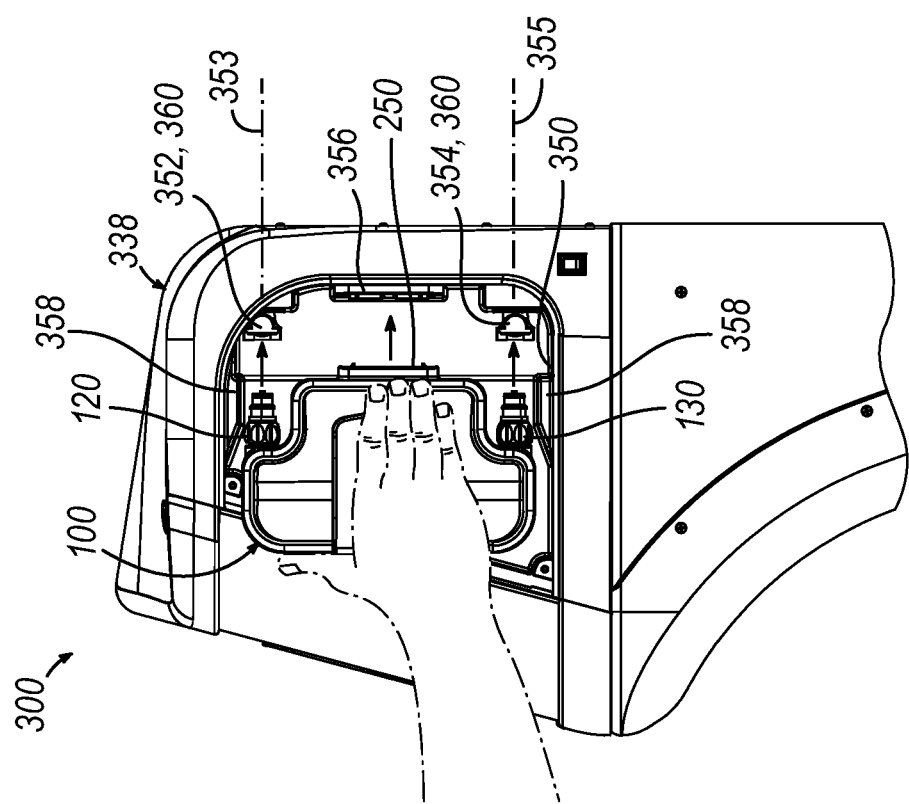
FIG. 13 illustrates plugging and unplugging of an aqueous ozone generator of the illustrative embodiment with a docking station of the aqueous ozone sanitizing device of FIGS. 1A and 1B.
Figure 15:
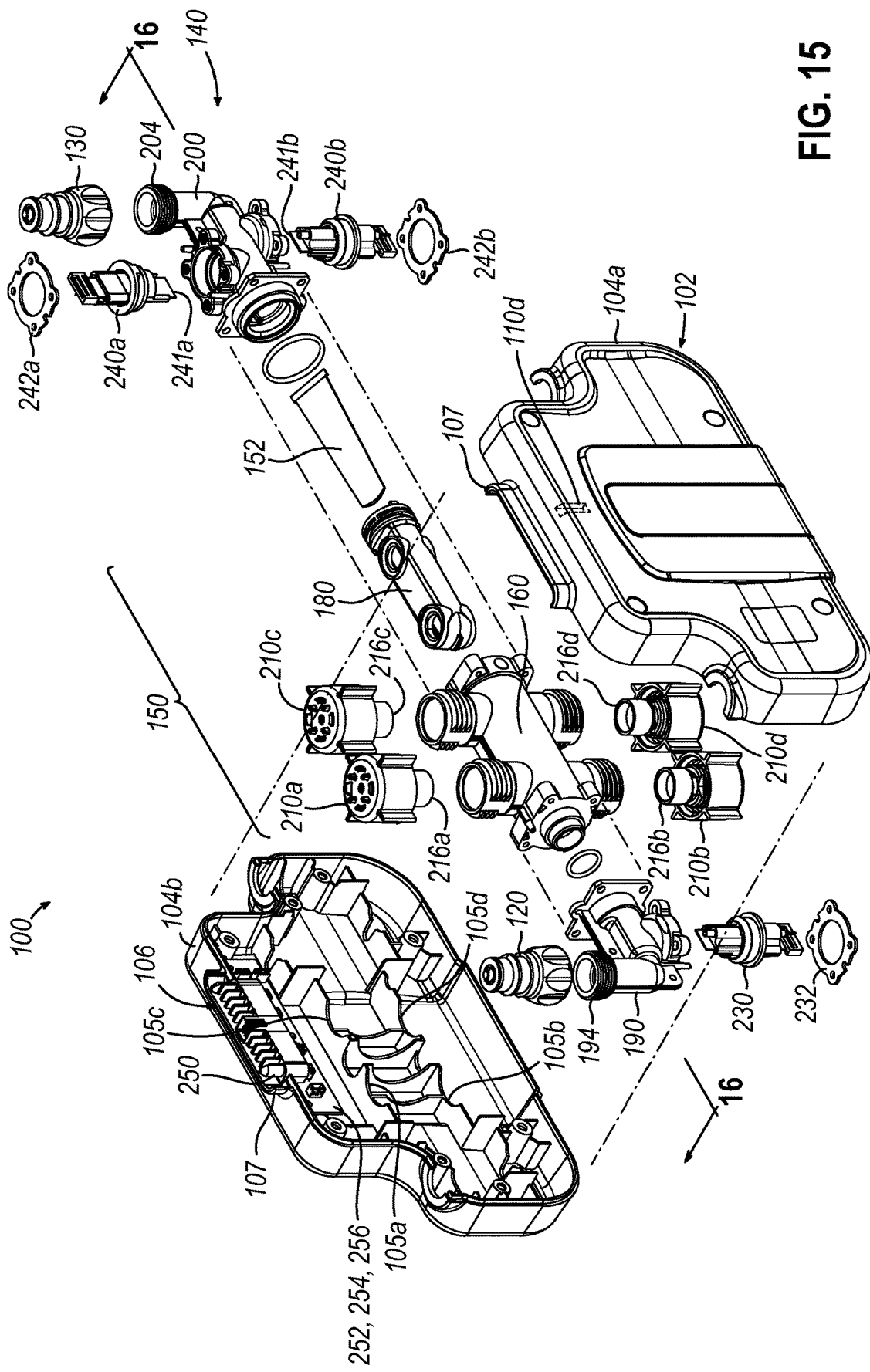
FIG. 15 illustrates an exploded view of the aqueous ozone generator of FIG. 13.
Figure 16:
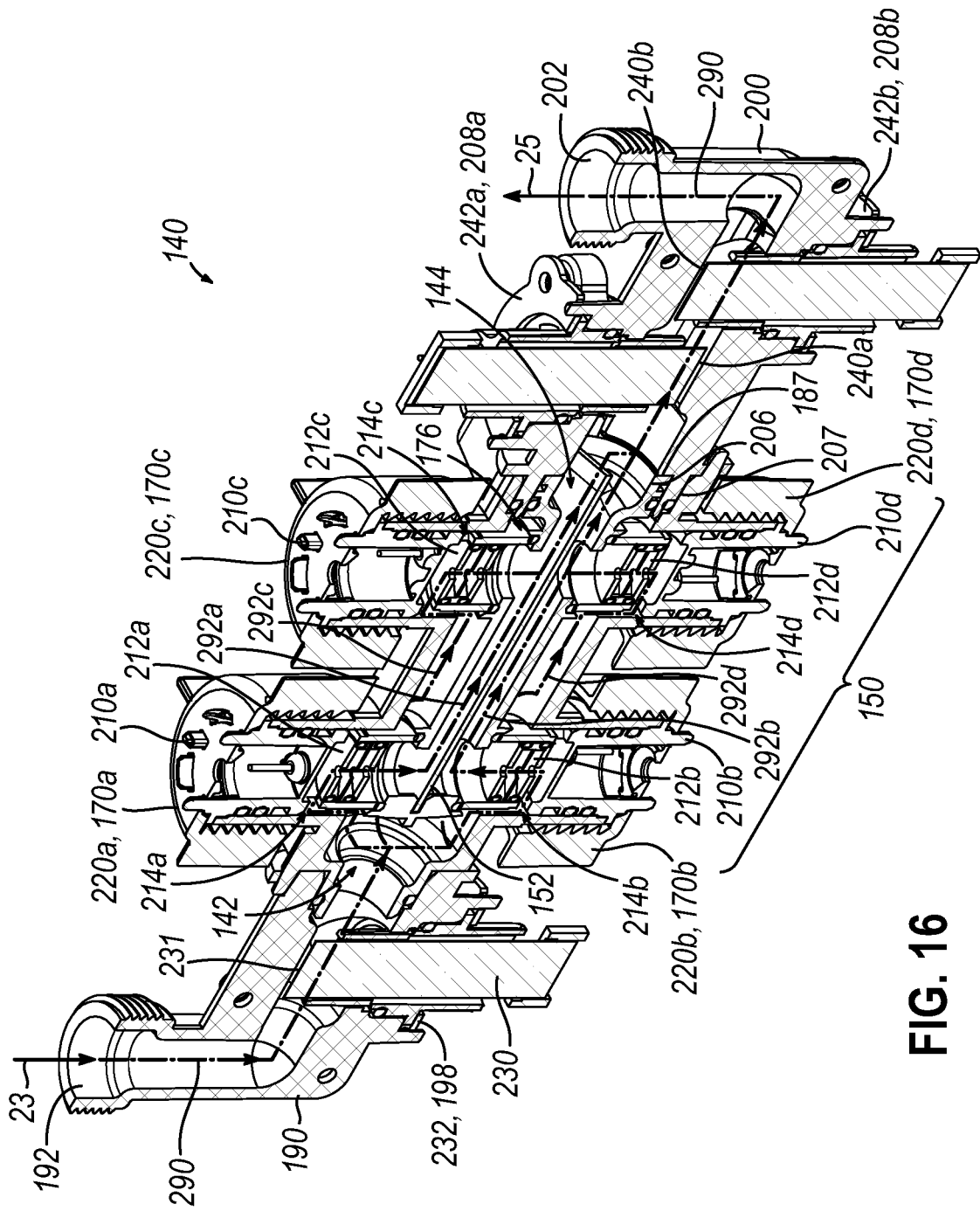
FIG. 16 illustrates a cross-sectional view of a manifold portion of the aqueous ozone generator of FIG. 15 taken along cutting plane line 16-16 shown in FIG. 15.

Referring to FIGS. 15 and 16, an illustrative aqueous ozone generator 100 used with a aqueous sanitizing system according to the present disclosure, including with the hand sanitizer 300, is illustrated. Referring to FIGS. 13 and 14, the aqueous ozone generator 100 includes features described below that enable it to be plugged into the docking receptacle 350, also referred to a docking station, of the hand sanitizer 300 in a single movement along a single axis. For example, not requiring rotation or twisting of the aqueous ozone generator 100 or other components to fluidly and electrically engage and mechanically lock the aqueous ozone generator 350 with the docking receptacle 350. While some prior art designs disclose individual generator cells and individual sensors capable of being unscrewed and replaced from a prior art system, aqueous ozone generator 100 advantageously can provide one or more generator cells 210, sensors, and other electronic and mechanical devices discussed below in a single housing 102 and pluggable, docking form that can be removed and replaced with exposing sensitive surfaces of the components to potential damage upon removal or installation as in prior art systems.

Referring to FIGS. 15 and 16, the aqueous ozone generator 100 receives untreated water supply 50 at a water inlet connector 120 and provides ozonated water 52 at a water outlet connector 130. An electrical connector 250 connects power signals 260, sensor data signals 262, security data signals 264, and data logging signals 266, as will be described further below, with the hand sanitizer 300. The connectors 120, 130, and 250 may be, for example, plastic and/or metal quick-disconnect connectors to facilitate the pluggable aspect of the generator 100, including auto-locking of mechanical features to retain the engaged position. The hand sanitizer 300 include associated connectors 352, 354, and 356 within the docking receptacles 350.

Referring to FIG. 15, the generator 100 is shown in exploded perspective view. Referring to FIG. 16, a manifold 140 of generator 100 is shown in an assembled cross-sectional view. The manifold 140 that forms a water passageway 290 for waterflow and treatment between an inlet opening 192, at which the connector 120 may be attached, and an outlet opening 202, at which the connector 130 may be attached. The manifold 140 also mounts and fluidly couples with the water passageway 290 several water treatment devices 110, 230, and 240.

In the illustrative embodiment the manifold 140 and the water passageway 290 include a central water passageway portion 150 that is fluidly coupled between an inlet waterway passage portion 190 and an outlet water passageway portion 200. In the illustrative embodiment of the generator 100, ozone generating cells 210a-210d are mounted upon and fluidly coupled with the central water passageway portion 150, an inlet sensor 230 is mounted upon and fluidly couples with inlet water passageway portion 190, and outlet sensors 240a and 240b are mounted upon and fluidly coupled with the outlet water passageways portion 200.

In the illustrative embodiment, an untreated supply waterflow 23 provided to the generator 100 by water supply connector 352 flows through an operably fixed (i.e., continuous, without valves or other actuators that operably change the flow) water passageway 290 formed by manifold 140, ultimately exiting as ozonated water 52 at an outlet opening 202 of the outlet water passageway portion 200 and supplied to the ozonated water connector 354. As will be further discussed below, the operably fixed water passageway 290 includes a parallel flow water passageways 292a-d that are enabled in part by a coaxial feature of the central water passageway portion 150.

An electrical connector 250 that is coupled with electrical connector 356 is accessible from outside of the housing 102 and can be electrically coupled to or mounted to a circuit board 252. The circuit board 252 may include, for example, a memory device 254 and related electrical components, and a security device 256, which may be separate from or a function of the memory device 254. In the illustrative embodiment, controller 512, including generator circuits 540, send/receives power signals 260 and sensor data signals 262 with the generator 100; however, in an alternative embodiment, circuit board 252 may comprise these elements.

An inlet sensor 230 sensor provides measurement of an attribute, e.g. a property or parameter, of the untreated supply waterflow 23 that will be altered by the ozone generating cells 210 effecting an increase in ozone concentration in the waterflow through the water passageway 290. For example, inlet sensor 230 may be an oxidation reduction potential (ORP) sensor that provides a baseline measurement to controller 512 that can be compared to a measurement of the same property/parameter provided of the ozonated water 52 flow out of water passageway portion 150 of the manifold 140.

A change in oxidation-reduction potential (ORP) can be attributed to an increase in the ozone concentration in the water. An ozone concentration level can be determined by measuring the ORP downstream of the ozone generating cells 210a-d, and taking into account the ORP of the untreated water supply if known and consistent, or by actually measuring and taking into account the ORP upstream of the ozone generating cells 210a-d. The ozone concentration added to the water by the ozone generating cells 210a-d can be calculated as a function of the differential in upstream and downstream ORP measurements.

The inlet sensor 230 can comprise at least a pair of electrodes, a working electrode and a reference electrode, or alternatively, a set of three electrodes, a counter electrode, a working electrode, and a reference electrode, carried by one or more non-conductive substrates, such as silicone or glass, supported by a housing and exposed to the waterflow. The reference electrode uses an inert metal, for example, gold, platinum, silver or a chloride molecule thereof, which resist chemical action and corrosion, but will lose electrons to an oxidant such as ozone until its potential reaches that of the ORP level of the water. By comparing a constant potential established between the working electrode and counter electrode pair, which is not affected by change in ORP, with the potential of the reference electrode, which is, the ORP of the water is determined. The conversion from difference in potential to the concentration of ozone can be made based on a calibration factor or look up table for the electrode set developed using a solution of known ozone concentration.

The sensor 230 and sensor 240a-b discussed below may be, for example, one of the sensor configurations disclosed by US Patent Publication 2016/0209346 published Jul. 21, 2016, which is hereby incorporated herein by reference, or the commercially available electrode sensor part numbers such as RRPX020AU and RREFX103 or RRPE100XC and RRPEAGCL from Pine Research of Durham, N.C.

In some embodiments, sensors 230 and 240a-b may additionally or alternative include sensing elements on a single or multiple substrates for temperature, flow, conductivity, acidity, and other such attributes of water.

Referring to FIG. 16, a flow separation chamber 142 is defined by the central water passageway portion 150. In the illustrative embodiment, the waterway passageway portion 150 includes an internal conduit 180 located coaxially within outer conduit 160, thereby defining a coaxial arrangement and parallel flow feature of manifold 140. The functions of the central water passageway portion 150 include exposing the waterflow through water passageway 290 to the ozone generating cells 210a-d, thereby increasing the ozone concentration of the waterflow, and minimizing the length of water passageway 290 and minimizing changes in water pressure, velocity, vortices, and other flow disturbances, all of which all to the reduce ozone concentration of the waterflow.

Each ozone generating cell 210a-d includes a generating portion 212a-d as well as a housing, fluid pathways, and/or other support structure. An exemplary generating portion 212a-d includes a pair of electrode plates (an anode and a cathode) having slots defined therethrough for the flow of water, hydrogen, oxygen, and ozone. The electrodes can be constructed of boron-doped silicone and coated with boron-doped diamond, for example, using chemical vapor deposition. Power can be applied from all edges of the electrodes to maximize ozone production. The electrodes can be separated by a thin membrane that allows proton exchange therethrough, and for example a solid polymer electrolyte such as a polytetrafluoroethylene (PTFE)/perfluorosulfonic acid (PFSA) copolymer membrane, which is commercially available from The Chemours Company of Wilmington, Del. as NAFION (trademark of The Chemours Company FC, LLC).

As is discussed further below, each of the parallel water passageways 292a-d of the present disclosure can provide a waterflow across each oppositely charged electrode plate, for example, across the electrode surface on the side opposite the separation membrane, resulting in the production of ozone within the water. The thin separation membrane located between electrode plates, for example, 20-30 microns thick, may also allow for some cross-diffusion of water, hydrogen, and oxygen molecules.

The concentration of ozone developed by the generating cell is a function of the level of power supplied to the electrolytic generating cell by generator circuits 540. In particular, by controller 512 controlling the current supplied to each ozone generating cell, the concentration of ozone can by controlled. In the illustrative embodiment, the concentration of ozone controlled by hand sanitizer 300 via the individual power signals 260 provided by generator circuits 540, through connectors 356 and 250 and connected through to each respective ozone generating cell 210a-d.

An example of an ozone generating cell 210 suitable for use in generator 100 for generating aqueous ozone is an electrolytic cell, for example, as disclosed by U.S. Pat. No. 10,640,878 issued on May 5, 2020, which is hereby incorporated herein by reference; however, alternative or improved ozone generating cells known in the art are also contemplated for use in generator 100. Exemplary electrolytic ozone generating cells 210 provide a mechanical structure to guide a water flow across the surfaces of a perforated pair of electrodes, an anode and a cathode each framed by a current spreader, and separated by a proton exchange membrane (PEM) designed to conduct protons between the anode and cathode. An exemplary electrode can be constructed of boron-doped silicon or another suitable material. The boron doped silicon material serves as a conductor to pass current between the current spreader and boron doped, The doped silicon material may be about 200-800 microns thick, such as about 500 microns thick. The front side each electrode may have a boron-doped diamond coating or another suitable coating. The coating may be about 2-10 microns thick. The coating may be applied to the underlying silicon material by chemical vapor deposition (CVD) or another suitable deposition technique. The illustrative electrodes can be rectangular in shape, for example, having a width of about 8 millimeters and a length of about 10 millimeters, although the size and shape of the electrodes may vary, and are available from Neocoat SA of La Chaux-de-Fonds, Switzerland.

The PEM may be constructed of a solid polymer electrolyte (SPE) membrane, for example, polytetrafluoroethylene (PTFE)/perfluorosulfonic acid (PFSA) copolymer membrane, which is commercially available from DuPont™ as a Nafion® membrane.

The arrangement of the various components of central water passageway portion 150 and ozone generating cells 210a-d divides the waterflow through the water passageway 290 into a number of water passageways 292a-d that is that same as the number ozone generating cells 210 installed with manifold 140. Each of the parallel water passageways 292a-d enter the inner conduit 180 through the respective cell opening 182 defined by the inner conduit.

Another function of the parallel water passageways 292a-d arrangement is that a higher ozone concentration can be achieve for the same flowrate through the water passageway 290 and power delivered to the ozone generating cells 210a-d than can be achieved for the same number of ozone generating cells 210a-d arranged in a serial water pathway arrangement. In the parallel arrangement, the water flowrate through each ozone generating cell 210a-d is divided by the number of cells/parallel water passageways 292a-d, for example, four for the illustrative embodiment. This provides the waterflow through each parallel water passageway with a higher ozone concentration than if the flowrate was four times as high. Although a serial arrangement should boost the ozone concentration at each successive ozone generating cells 210a-d, it has been found that the loss of ozone generated by early cells and flow through subsequent cells, for example, due to the waterflow experiencing added disturbances to the flow by the serial flow arrangement, reduces the efficacy of the cumulative serial effect in boost ozone concentration.

It is also thought that the parallel water passageways 292a-d arrangement can lengthen the duty life of the ozone generating cells 210a-d as each may be operated at a lower power to achieve the desired ozone concentration than if fewer cells were used, or if the cells were arranged serially. And if the desired ozone concentration can be achieved by powering a subset of the ozone generating cells, the duty life can be lengthened by alternating selectively powering only a subset of the cells. The later may also be used to keep a generator 100 in service that has suffer a degradation of failure of one of the ozone generating cells 210a-d as the load can be picked up by the remaining fully functional cells without changes to the hardware or water passageway 290.

In the illustrative embodiment of manifold 140, a flow confluence chamber 144 is defined adjacent a second end 187 of the inner conduit 180 and the inlet opening 206 of the outlet water passageway portion 200. Within the flow confluence chamber 144, the waterflows from the first and second flow chambers 188a-b, (separate parallel water passageway flows 292a-d) are recombined again into a single waterflow through water passageway 290 in the outlet water passageway portion 200.

The ozonate water 52 through the outlet water passageways portion 200 passes over the surfaces of sensors 240a-b, for example oxidation reduction potential sensors as is disclosed above. By comparing ORP of ozonated water 52 as measured by sensors 240a and 240b, with the untreated supply waterflow 23 as measured by sensor 230, the ozone concentration added to the water passageway 290 waterflow by the ozone generating cells 210 can be determined and ozone generating cells 210 can be individually and collectively controlled by controller 512 accordingly via power signals 260 provided by generator circuits 540 to achieve a desired ozone concentration. Alternatively, the inlet sensor 230 could be eliminated and untreated supply waterflow 23 by sensor 240a with waterflow provided without energizing ozone generator cells 210 to baseline ORP for later comparison with ORP of ozonated water 52 measured by sensor 240a when the ozone generator cells 210 are energized. Yet another alternative is to for gall all ORP sensors 230 and 240a/b and to control the desired aqueous ozone concentration by setting the current level know to produce the specific concentration desired for the configuration of the generator 100 for a given flow rate, for example, 410 milliamps, for 3 gph, to provide 0.8 ppm aqueous ozone for the illustrative embodiment.

With brief reference to FIGS. 1A and 4, the inlet water passageway portion 190 defines a connector mount 194 for coupling the inlet connector 120 to the manifold 140. For example, the connector mount 194 may be a threaded coupling, compression coupling, adhesive joint, or other known standard or non-standard fluid coupling known in the art and suitable for the selected type of the water inlet connector 120. The outlet water passageway portion 200 defines a corresponding connector mount 204 at outlet opening 202 for the water outlet connector 130.

An advantage of the generator 100 according to the present disclosure is how compactly ozone generating cells 210 and sensors 230 and 240 can be housed and coupled with the water passageway 290 for ozonating the waterflow. For example, by minimizing the length of the water passageway 290, losses in ozone concentration is minimized. One aspect of minimizing the length of the water passageway 290 is the coaxial arrangement of the central water passageway portion 150, including the parallel water passageways 292a-d arrangement that the coaxial arrangement enables. Another aspect of minimizing the length is locating more than one ozone generating cell 210 along the same circumferential arc 158 (defined by axes 156a-b), as illustrated in FIG. 7 and FIG. 8C. For example, cell mount coupling 170a is located at an angular axis 156a of +90 degrees along the circumferential arc 158, and cell mount coupling 170b is located at an angular axis 156b of −90 degrees along the circumferential arc 158.

The various components of the manifold 140 may be constructed, for example molded from rigid materials not susceptible to breakdown from water and ozone, for example, polysulfone (PSU), polyvinylidene fluoride (PVDF), or 40% glass fiber reinforced polyphenylene sulphide (PPS). In other embodiments, the manifold 140 may be comprised of a unitary structure or a structure divided into portions or subcomponents differently than is described herein for the illustrative embodiment and as may be desirable for manufacturing, assembly, operational or reconstruction.

The electrical connector 250 can be electrically coupled to or mounted directly to a circuit board 252. The circuit board 252 may include a memory device, for example for identification data for the generator 100 and/or the associated hand sanitizer 300, or both, including for example a serial and/or model number and/or compatibility information between generators 100 and sanitizers 300, and pairing of a specific serial number generator with a specific serial number sanitizer. Additionally, the memory device 254 may enable data logging of usage, including lifespan, error detection, and information concerning individual instances of use by personnel. Lifespan data may include calibration information, specifications, elapsed or remaining usage of individual ozone generating cells 210 and/or the generator 100, including based on, for example, hours, gallons of water, ozone volume, total power, and the like.

Data logging may include transmission of usage information through electrical connector 250 to controller 512 for storage on memory 518 or for transmission to a personal computing device and/or remote server 80. Additionally, a security device 256 be included as a separate device, or as a feature of the memory device 254. Security device 256 may include encryption, blockchain, or other secure feature to authenticate the source of manufacturing, or reconstruction of the generator 100, or the pairing of generator 100 with a particular hand sanitizer 300 or other connected devices.

The electrical connector 250 and circuit board 252 an receive power signals 260 for driving the ozone generating cells 210a-d, powering the sensors 230 and 240a-b, and for sending sensor data signals 262 from the sensors, and for sending and/or receiving security data signals 264 and logging data signals 266. In one embodiment, circuit board 252 includes a processor for providing control, security, data logging, or other functionality recited herein or otherwise known to a person of ordinary skill in the art for manufacturing, operating, repairing, and reconstructing the generator 100.

Referring to FIG. 15, reconstruction of an expended generator cartridge 100 can include, for example, separating housing 102, removing and replacing all degraded components, for example, generator cells 210 and/or sensors 230 and 240, cleaning those and other remaining components that can be reused, replacing remaining components as required, reassembly and closing housing 102, rewriting memory and security devices 252, 254, 256, and calibration and/or testing, for example, verifying that the reconstructed generator 100 provides the desired aqueous ozone 25 concentration for water 23 provided at a given flowrate with the expected current and voltages levels for each of the generator cells 120, including proper operation of any sensors 230 and 240.

Referring to FIGS. 13 and 14, plug-in coupling of the generator 100 into a corresponding docking receptacle 350 of the hand sanitizer 300 requires proper orientation to ensure that the electrical connector 250 and the water inlet connector 120 and water outlet connector 130 are not reversed with the corresponding connectors 352, 354, and 356 of the docking receptacle. One or both of generator 100 and the docking receptacle 350 can include orientation features that prevent coupling if the orientation is incorrect. For example, a guidance and orientation feature 110d (FIG. 15) at a first end of the housing 102, in this example a recess or a protrusion. Corresponding guidance and orientation features 358 (FIG. 13) of the docketing receptacle 350 are interoperable with orientation feature 110d or operate in addition to prevent plugging of the generator 100 into the docking receptacle 350 unless oriented and/or positioned correctly to result in proper water and electrical connections.

Alternatively, different size, shape, or other configuration of the water inlet connector 120 and the water outlet connector 130 and their associated connectors 352 and 354 of the docking receptacle 350 can be used to prevent a ensure proper orientation and prevent a reverse connection. Similarly, oriented features of the electrical connectors 250 and 356 could alternative be used to ensure correct orientation. Housing 102 may also define recesses, for example orientation features 110d (FIG. 15) to additionally or alternative operate with features of the docking station 350 to prevent improper orientation and review connections.

Referring to FIG. 13, to enable plugging and unplugging generator 100 into the docking receptacle 350 using a singular axis motion, the water connectors 120 and 353 are fixed respectively in housing 102 and docking receptacle 350 to define a common longitudinal axis 353 that is displaced laterally and oriented parallel with a common longitudinal axis 355 of the water connectors 130 and 354. A connection axis of the electrical connectors 250 and 356 is also parallel to the longitudinal axes 353 and 355.

Advantageously, each of the three pair of connectors, 120 and 352, 130 and 354, and 250 and 356 are selected to enable pluggable engagement using a singular axis of motion along longitudinal axes 353 and 355 to engage all of the corresponding connectors simultaneously and without further action other than moving the generator manually into position along the referenced parallel axes. For example, the generator can be held and moved into position to connect the three connector pairs without manually manipulating each or any of the connectors 120 and 352, 130 and 354, and 250 and 356.

Additionally, and advantageously, a locking mechanism 116 of the generator 100 can operably cooperate with a locking mechanism 360 of the docking receptacle 350 so that generator 100 auto-locks into position relative to the docking receptacle 350, ensuring corresponding connectors remain engaged. Referring to FIGS. 14A and 14B, a release mechanism 362a associated with the docking receptacle or a release mechanism 118 associated with the generator 100 can be manually actuated to disengage locking mechanisms 116 and 360. The connector pairs used for 120 and 352 and/or 130 and 354 can be selected to be auto-locking fluid connectors as are known in the art.

For example, the water connector 352 may include locking clips that springs into position to engagingly interfere with an engagement feature 126 of the water inlet connector 120 to fluidly couple the connectors 352 and 120 until manually released by the release mechanism 362a which can move the locking clips to a disengaged position, allowing the generator 100 to be pulled along axes 353 and 355, disengaging the connector pairs and allowing the generator 100 to be removed from the docking receptacle 350 and be replaced with a new or a reconstructed generator 100. For example, commercially available connectors such as part numbers HFCD261235BSPP and HFCD16835 available from Colder Product Company of Saint Paul, Minn.

Because of the pressure provided by untreated water supplies 50 varies significantly with local utility and building infrastructure, to ensure sufficient pressure and flowrate of untreated water required for correct operation of the hand sanitizer 300, an untreated water holding tank 614 can be included to receive an accumulate water from the untreated water supply for subsequent sanitizing cycles, and the water pump 622 can be provided with the sanitizer to deliver the desired flowrate from the holding tank to the generator 100 of about 3.0 gallons per minute at a supply pressure entering the generator 100 of about 60 psi, a typical pressure available in municipal water supplies. An illustrative holding tank 614 provides capacity for more than one full sanitizing cycle, for example, at least two cycles, for example, at least about 1.8 gallons. An illustrative water pump 622, for example, a self-priming diaphragm pump, provides a capacity of up to 5.5 gallons per minute and maximum pressure of 70 psi. In an alternative embodiment, other compensating flow rate restrictor(s) may be used to provide the desired flow rate and pressure. An example fan 560 provides 155 cubic feet per minute of airflow. An example ozone filter 348 is an activated carbon filter sized about 15.5 cubic inches. Alternative or additional filter material for filter ozone out of the exhaust airflow include catalysts such as manganese dioxide and copper dioxide.

An embodiment of the present disclosure may also include additional and/or alternative features and details as in known in the art for aqueous ozone systems, for example, as disclosed by US Patent Publication No. 2019/0001006 published Jan. 3, 2019, and hereby incorporated by reference herein.

While the invention has been illustrated and described in detail in the foregoing drawings and description, the same is to be considered as illustrative and not restrictive in character, it being understood that only illustrative embodiments thereof have been shown and described and that all changes and modifications that come within the spirit and scope of the invention as defined in the claims and summary are desired to be protected.

| REFERENCE NUMERAL LISTING | |
|---|---|
| 20a-b | user's hands |
| 22 | lateral-medial axis |
| 23 | lateral-medial rotation |
| 24 | anterior-posterior axis |
| 25 | anterior-posterior rotation |
| 26 | proximal-distal axis |
| 30 | wrist |
| 32 | central |
| 34 | palm side |
| 36 | dorsal side |
| 38 | fingers |
| 40 | thumb/lateral |
| 42 | medial (little finger) |
| 44 | forearm |
| 50 | untreated water supply |
| 52 | ozonated water |
| 70 | WAN |
| 80 | server |
| 82 | personal computing device |
| 100a-b | aqueous ozone generator |
| 102 | housing |
| 104a-b | housing side |
| 105a-b | component supports |
| 116 | locking mechanism |
| 118 | release mechanism |
| 120 | water inlet connector |
| 122 | opening |
| 126 | engagement feature |
| 130 | water outlet connector |
| 132 | opening |
| 136 | engagement feature |
| 140 | manifold |
| 142 | flow separation chamber |
| 144 | flow confluence chamber |
| 150 | coaxial water passageways portion |
| 152 | baffle/divider |
| 170a-d | cell mount coupling |
| 172a-d | cell coupling opening |
| 176 | annulus |
| 180 | inner conduit |
| 181 | first end |
| 187 | second end |
| 188a-b | first/second flow chamber |
| 190 | inlet water passageways portion |
| 192 | inlet opening |
| 194 | connector mount |
| 196 | outlet opening |
| 197 | outlet coupling |
| 198 | sensor coupling |
| 200 | outlet water passageways portion |
| 202 | outlet opening |
| 204 | connector mount |
| 206 | inlet opening |
| 207 | inlet coupling |

-continued

| REFERENCE NUMERAL LISTING | | |
|---|---|---|
| 208a-b | sensor couplings | |
| 209b | sensor alignment feature | |
| 210a-d | ozone generating cells | |
| 212 | generating portion | |
| 220a-d | mount coupling | |
| 230 | inlet sensor | |
| 231 | sensor element | |
| 232 | coupling | |
| 240a-b | outlet sensors | |
| 241a-b | sensor elements | |
| 242a-b | mounting coupling | |
| 250 | electrical connector | |
| 252 | circuit board | |
| 254 | memory device | |
| 256 | security device | |
| 258 | connection axis | |
| 260 | power signal | |
| 262 | sensor data signal | |
| 264 | security data signal | |
| 266 | logging data signal | |
| 290 | water passageway | |
| 292a-d | parallel water passageways | |
| 300 | aqueous ozone hand sanitizer | |
| 310 | sanitizing chamber/hood | |
| 312 | chamber upper half | |
| 314 | chamber top | |
| 316 | top contours | |
| 320 | chamber lower half | |
| 322 | chamber bottom | |
| 324 | bottom contours | |
| 325 | drain | |
| 326 | left side | |
| 328 | right side | |
| 330 | housing chassis | |
| 332 | lower frame | |
| 334a | lower portion | |
| 334b | counter top upper portion | |
| 336 | cover/hood | |
| 338 | cover frame | |
| 340 | left cover | |
| 342 | right cover | |
| 344 | top cover | |
| 346 | fan screen | |
| 348 | ozone filter | |
| 350a-b | docking receptacle/station | |
| 352 | water supply outlet connector | |
| 353 | supply longitudinal axis | |
| 354 | ozonated water inlet connector | |
| 355 | ozonated longitudinal axis | |
| 356 | electrical connector | |
| 358 | orientation/alignment feature | |
| 360 | locking mechanism | |
| 362 | release mechanism | |
| 370 | front cover | |
| 372a-b | openings | |
| 374 | horizontal axis | |
| 376 | vertical axis | |
| 380 | center | |
| 382 | opening vertical span | |
| 384 | opening horizontal span | |
| 386 | opening spacing | |
| 390 | channel | |
| 392 | channel vertical span | |
| 394 | rim | |
| 396 | horizontal marking feature | |
| 398 | vertical marking feature | |
| 400 | spray system | |
| 402a-b | manifold | |
| 404a-b | pressure sensor | |
| 406a-b | flow meter | |
| 410a-e | left spray devices/delivery outlets | |
| 411 | fluidic oscillator | |
| 412 | device longitudinal axis | |
| 413 | rotational displacement angle | |
| 414a | upper rotational displacement span | |
| 414b | lower rotational displacement span | |
| 415 | rotational displacement angle | |

-continued

| REFERENCE NUMERAL LISTING | | |
|---|---|---|
| 416a | upper rotational displacement span | |
| 416b | lower rotational displacement span | |
| 417 | proximal-distal axis | |
| 418 | anterior-posterior axis | |
| 419a-b | spray fan angular displacement | |
| 420 | left spray/application zone | |
| 421a-e | device spray pattern | |
| 424 | lateral-medial axis | |
| 430a-e | right spray devices/delivery outlets | |
| 431 | anterior-posterior datum plane | |
| 432 | anterior-posterior location | |
| 433a | proximal-distal location datum plane | |
| 433b | proximal-distal angular datum plane | |
| 434 | proximal-distal location | |
| 435a | lateral-medial location datum plane | |
| 435b | laterial-medial angular datum plane | |
| 436 | laterial-medial location | |
| 440 | right spray/applicaton zone | |
| 441 | lateral-medial zone center | |
| 442 | anterior zone edge | |
| 443 | zone anterior-posterior span | |
| 444 | zone anterior-posterior slope | |
| 446 | proximal zone edge | |
| 447 | zone lateral-medial span | |
| 448 | zone lateral-medial slope | |
| 449 | zone proximal-distal span | |
| 500 | control system | |
| 510 | power supply | |
| 512 | controller | |
| 514 | power regulator | |
| 516 | processor | |
| 518 | memory | |
| 520 | WAN/LAN transceiver | |
| 522 | onboard transceiver | |
| 524 | pump controller | |
| 526 | valve controller | |
| 528 | sensor controller | |
| 540 | generator controllers | |
| 542 | driver | |
| 544 | power monitor | |
| 546 | polarity swap | |
| 548 | sensor circuit | |
| 560 | fan | |
| 562 | gaseous ozone sensor | |
| 580 | ID reader | |
| 582 | presence sensor | |
| 584 | user interface | |
| 586 | lighting | |
| 588 | UV light | |
| 590 | hand sensors | |
| 600 | water supply system | |
| 610 | supply valve | |
| 612 | inlet filter | |
| 614 | holding tank | |
| 616 | water level sensor | |
| 618 | drain valve | |
| 620 | temperature sensor | |
| 622 | pump | |
| 624 | flow meter | |
| 626 | pressure sensor | |
| 628 | releasable coupling | |
| 700 | sanitizing process | |

The invention claimed is:

1. An aqueous ozone sanitizer, comprising:
a sanitizing chamber for dispensing aqueous ozone onto a user's hands;
a left plurality of spray devices coupled to the sanitizing chamber configured to simultaneously irrigate a user's entire left hand positioned within a left spray zone of the chamber, the left plurality of spray devices including at least a first left-upper spray device located above the left spray zone and at least a first left-lower spray device located below the left spray zone;

a right plurality of spray devices coupled to the sanitizing chamber configured to simultaneously irrigate a user's entire right hand positioned within a right spray zone of the chamber, the right plurality of spray devices including at least a first right-upper spray device located above the right spray zone and at least a first right-lower spray device located below the right spray zone;

at least a first and a second aqueous ozone generator coupled to the sanitizing chamber;

and wherein:
- a first subset of a set consisting of the left plurality of spray devices and the right plurality of spray devices is fluidly coupled to the first aqueous ozone generator;
- a second subset of the set is fluidly coupled to the second aqueous ozone generator; and
- whereby the position of the first and the second aqueous ozone generators relative to the left and right plurality of spray devices and a selection of the first subset and the second subset minimizes the distance between each of the left and the right plurality of spray devices and the one of the first and the second aqueous ozone generators to which it is fluidly coupled, thereby minimizing a depletion of ozone concentration between the first and the second aqueous ozone generators and the left and the right plurality of spray devices.

2. The aqueous ozone sanitizer of claim 1, wherein:
the first aqueous ozone generator is positioned adjacent the left plurality of spray devices;
the first subset includes all the left plurality of spray devices;
the second aqueous ozone generator is positioned adjacent the right plurality of spray devices; and
the second subset includes all the right plurality of spray devices.

3. The aqueous ozone sanitizer of claim 1, wherein:
the first aqueous ozone generator is positioned adjacent the first left-upper spray device and the first right-upper spray device;
the first subset includes the first left-upper spray device and the first right-upper spray device;
the second aqueous ozone generator is located adjacent the first left-lower spray device and the first right-lower spray device; and
and the second subset includes the first left-lower spray device and the first right-lower spray device.

4. The aqueous ozone sanitizer of claim 1, further comprising: a housing for the sanitizing chamber defining at least one opening to receive the user's left and right hands; and
wherein the housing defines at least one of a horizontal marking feature and a vertical marking feature for each of the user's left and right hands, thereby providing a guide to instruct an insertion point of the user's left and right hands through the at least one opening and into the corresponding ones of the left and the right spray zones.

5. The aqueous ozone sanitizer of claim 1, further comprising:
a housing for the sanitizing chamber defining a pair of openings to receive each of the user's left and right hands, each of the pair of openings defining an opening vertical span and an opening horizontal span; and
wherein the opening vertical span is greater than the opening horizontal span, thereby instructing and guiding the user's hands into a vertical orientation upon insertion through each of the openings.

6. The aqueous ozone sanitizer of claim 5, wherein the ratio of the opening horizontal span to the opening vertical span is less than 3:4.

7. The aqueous ozone sanitizer of claim 5, wherein the ratio of the opening horizontal span to the opening vertical span is about 2:3.

8. The aqueous ozone sanitizer of claim 5, wherein the ratio of the opening horizontal span to the opening vertical span is less than 2:3.

9. The aqueous ozone sanitizer of claim 5, wherein the sanitizing chamber housing further defines a channel connecting the pair of openings, the channel defining a channel vertical span smaller than the opening vertical span.

10. The aqueous ozone sanitizer of claim 9, wherein the ratio of the channel vertical span to the opening vertical span is less than 3:4.

11. The aqueous ozone sanitizer of claim 9, wherein the ratio of the channel vertical span to the opening vertical span is about 2:3.

12. The aqueous ozone sanitizer of claim 9, wherein the ratio of the channel vertical span to the opening vertical span is less than 2:3.

13. The aqueous ozone sanitizer of claim 1, wherein
the left plurality of spray devices further includes a second left-upper spray device and a second left-lower spray device; and
a right plurality of spray devices further includes a second right-upper spray device and a second left-lower spray device.

14. The aqueous ozone sanitizer of claim 13, wherein:
the left spray zone is defined by a bounded area of irrigated space provided by the positions, orientations, and overlapping spray patterns of the left plurality of spray devices; and
the right spray zone is defined by a bounded area of irrigated space provided by positions, orientations, and overlapping spray patterns of the right plurality of spray devices.

15. The aqueous ozone sanitizer of claim 14, wherein:
the positions, orientations, and overlapping spray patterns of the left plurality of spray devices provide simultaneously irrigation of the entire left hand of the user when oriented with the user's left palm facing the user's right hand; and
the positions, orientations, and overlapping spray patterns of the right plurality of spray devices provide simultaneously irrigation of the entire right hand of the user when oriented with the user's right palm facing the user's left hand.

16. The aqueous ozone sanitizer of claim 15, wherein each of the left and right spray zone encompasses less than 320 cubic inches.

17. The aqueous ozone sanitizer of claim 15, wherein each of the left and right spray zones span between about 3.5 to about 4.5 inches along an anterior-posterior axis, span about 8 inches along an lateral-medial axis, and span about 10 inches along a proximal-distal axis.

18. The aqueous ozone sanitizer of claim 15, further comprising a housing for the sanitizing chamber, the housing defining a pair of openings to receive each of the users left and right hands, and wherein each of the left and right spray zones define a proximal-distal axis that is oriented to about 15 degrees sloped downwardly in a direction extending from the pair of openings into the sanitizing chamber.

19. The aqueous ozone sanitizer of claim 15, wherein each of the left and right spray zones define a lateral-medial axis that is oriented to between about 10 degrees and 25 degrees sloped outwardly in a direction extending from the bottom toward the top of sanitizing chamber.

20. The aqueous ozone sanitizer of claim 13, wherein a displacement in angular alignment of a central axis of spray between each of the first upper-right spray device and the second upper-right spray device is between 30 degrees to 50 degrees about each of an anterior-posterior axis and about a proximal-distal axis.

21. The aqueous ozone sanitizer of claim 13, wherein a difference in angular alignment of a central axis of spray between each of the first lower-right spray device and the second lower-right spray device is between 0 degrees to 10 degrees about each of an anterior-posterior axis and about a proximal-distal axis.

22. The aqueous ozone sanitizer of claim 13, wherein each of the left and each of the right plurality of spray devices each define at least one fluidic oscillator providing a spray pattern for each spray device spanning about 16 degrees about a first axis and spanning about 32 degrees about a second axis which is perpendicular to the first axis.

23. An aqueous ozone sanitizer, comprising:
a sanitizing chamber for dispensing aqueous ozone onto a user's hands;
a left plurality of spray devices coupled to the sanitizing chamber and located and oriented to simultaneously irrigate a user's entire left hand positioned within a left spray zone of the chamber;
a right plurality of spray devices coupled to the sanitizing chamber and located and oriented to simultaneously irrigate a user's entire right hand positioned within a right spray zone of the chamber;
a first aqueous ozone generator located adjacent to and fluidly coupled to the left plurality of spray devices;
a second aqueous ozone generator located adjacent to and fluidly coupled to the right plurality of spray devices; and
whereby the position of the first and the second aqueous ozone generators relative to the left and right plurality of spray devices minimizes a depletion of ozone concentration between the first and the second aqueous ozone generators and the left and the right plurality of spray devices.

24. The aqueous ozone sanitizer of claim 23, wherein:
a first spray device of the left plurality of spray devices is positioned laterally of the left hand and is further positioned and oriented to irrigate a dorsal side of a metacarpal region and phalangeal region of the left hand;
a second spray device of the left plurality of spray devices is positioned laterally of the left hand and is further positioned and oriented to irrigate a dorsal side of a phalangeal region of the left hand;
a third spray device of the left plurality of spray devices is positioned medially of the left hand and is further positioned and oriented to irrigate an anterior side of the carpus region and the metacarpal region of the left hand; and
a fourth spray device of the left plurality of spray devices is positioned medially of the left hand and is further positioned and oriented to irrigate an anterior side of the phalangeal region of the left hand.

25. The aqueous ozone sanitizer of claim 24, wherein the fourth spray device of the left plurality of spray devices is further position and oriented to also irrigate an anterior side of the metacarpal region of the left hand.

26. The aqueous ozone sanitizer of claim 24, wherein:
the first spray device of the left plurality of spray devices is further position and oriented to also irrigate an anterior side of at least one of the metacarpal region and the phalangeal region of the left hand;
the third spray device of the left plurality of spray devices is further position and oriented to also irrigate a dorsal side of at least one of the carpus region and the metacarpal region of the left hand; and
the fourth spray device of the left plurality of spray devices is further position and oriented to also irrigate a dorsal side of at least one of the phalangeal region of the left hand.

27. The aqueous ozone sanitizer of claim 24, wherein the fourth spray device of the left plurality of spray devices is further position and oriented to also irrigate the metacarpal region of the left hand.

28. The aqueous ozone sanitizer of claim 24, wherein the left plurality of spray devices further comprises a fifth spray device positioned laterally of the left hand and further positioned and oriented to irrigate an anterior side of the carpus region and the metacarpal region of the left hand.

29. The aqueous ozone sanitizer of claim 23, further comprising:
a housing for the sanitizing chamber defining a pair of openings to receive each of the user's left and right hands, each of the pair of openings defining an opening vertical span and an opening horizontal span; and
wherein the opening vertical span is greater than the opening horizontal span, thereby instructing and guiding the user's hands into a vertical orientation upon insertion through each of the openings.

30. The aqueous ozone sanitizer of claim 23, wherein each of the left and each of the right plurality of spray devices each define at least one fluidic oscillator providing a spray pattern for each spray device, thereby loosening and lessening the microbe load by applying both chemical and mechanical rinsing and sanitizing action to the user's hands.

* * * * *